United States Patent [19]

DeGonia et al.

[11] Patent Number: 5,137,980
[45] Date of Patent: * Aug. 11, 1992

[54] ASHLESS DISPERSANTS FORMED FROM SUBSTITUTED ACYLATING AGENTS AND THEIR PRODUCTION AND USE

[75] Inventors: David J. DeGonia, Granite City; Paul G. Griffin, Collinsville, both of Ill.

[73] Assignee: Ethyl Petroleum Additives, Inc., St. Louis, Mo.

[*] Notice: The portion of the term of this patent subsequent to Dec. 10, 2008 has been disclaimed.

[21] Appl. No.: 801,488

[22] Filed: Dec. 2, 1991

Related U.S. Application Data

[63] Continuation-in-part of Ser. No. 524,422, May 17, 1990, Pat. No. 5,071,919, and a continuation-in-part of Ser. No. 762,453, Sep. 19, 1991.

[51] Int. Cl.$^5$ ................................................. C08F 8/32
[52] U.S. Cl. .................. 525/327.6; 525/329.5; 525/329.6; 525/379; 525/380; 525/382; 525/384; 525/327.7
[58] Field of Search ............... 525/327.6, 327.7, 329.5, 525/329.6, 379, 380, 382, 384

[56] References Cited

U.S. PATENT DOCUMENTS

| | | | |
|---|---|---|---|
| 3,215,707 | 11/1965 | Rense | 260/326.3 |
| 3,231,587 | 1/1966 | Rense | 260/346.8 |
| 3,382,172 | 5/1968 | Lowe | 252/42.7 |
| 3,476,774 | 11/1969 | Zaweski et al. | 260/346.8 |
| 4,152,499 | 5/1979 | Boerzel et al. | 526/52.4 |
| 4,234,435 | 11/1980 | Meinhardt et al. | 252/51.5 |
| 4,235,786 | 11/1980 | Wisotsky | 260/346.74 |
| 4,736,044 | 4/1988 | Hansen | 549/255 |
| 4,761,488 | 8/1988 | Fried | 549/255 |
| 4,883,886 | 11/1989 | Huang | 549/255 |
| 4,956,478 | 9/1990 | Fakoukakis et al. | 549/255 |

FOREIGN PATENT DOCUMENTS

| | | |
|---|---|---|
| 0317004 | 5/1989 | European Pat. Off. |
| 0355895 | 2/1990 | European Pat. Off. |
| 2904314 | 8/1980 | Fed. Rep. of Germany |
| 579283 | 11/1977 | U.S.S.R. |

Primary Examiner—Bernard Lipman
Attorney, Agent, or Firm—John F. Sieberth

[57] ABSTRACT

Succinimides, succinic esters, and succinic ester-amides are formed by
(A) reacting (i) at least one substantially aliphatic polymer of at least one lower olefin, and (ii) an acidic reactant or a mixture of two or more acidic reactants represented by the general formula $$R-CO-CH=CH-CO-R'$$

wherein R and R' are independently —OH, —O-lower alkyl, a halogen atom, or taken together are a single oxygen atom; the process being characterized in that:
a) the substantially aliphatic polymer is comprised predominantly or entirely of polyisobutene, at least 50% of the polyisobutene content of such polymer having an end group represented by the formula $$-CH_2-\underset{\underset{CH_3}{|}}{C}=CH_2$$

b) the mole ratio of said acidic reactant(s): said polymer(s) is at least 1:1;
c) the reaction mixture is maintained under superatmospheric pressure during at least a substantial portion of the reaction period; and
d) said acylating agent is characterized by having an average total tar rating as determined by the method described in the specification hereof that is at least 25% lower than the average total tar rating of a corresponding product made in the same way under the same reaction conditions using a polyisobutene containing up to 10% of the above-depicted end group; and
(B) reacting such acylating agent with at least one alcohol (preferably a polyhydric alcohol) or amine (preferably a polyamine having at least one primary amino group).

34 Claims, No Drawings

ASHLESS DISPERSANTS FORMED FROM SUBSTITUTED ACYLATING AGENTS AND THEIR PRODUCTION AND USE

REFERENCE TO RELATED APPLICATION

This is a continuation in part of our prior co-pending application Ser. No. 524,422 filed May 17, 1990, now U.S. Pat. No. 5,071,919 and Ser. No. 762,453, filed Sep. 19, 1991.

TECHNICAL FIELD

This invention relates to novel and eminently useful ashless dispersants formed from substituted acylating agents of the polybutenylsuccinic acid type, to novel and eminently useful methods for their production, and to novel and eminently useful compositions in which they are used.

BACKGROUND

Heretofore processes have been described for the thermal reaction between polybutenes (predominantly polyisobutenes) and maleic anhydride or like reactants whereby polybutenyl succinic anhydrides are formed. Some of the work along these lines is described, or at least referred to, for example in U.S. Pat. Nos. 3,018,247; 3,018,250; 3,018,291; 3,172,892; 3,184,474; 3,185,704; 3,194,812; 3,194,814; 3,202,678; 3,216,936; 3,219,666; 3,272,746; 3,287,271; 3,311,558; and in British Pat. No. 1 492 337. However as pointed out in U.S. Pat. Nos. 3,215,707 and 3,231,587, from the standpoint of commercial usefulness the alkylation of maleic anhydride with an olefinic hydrocarbon is very time-consuming and limited in its applicability to relatively low molecular weight olefinic hydrocarbon reactants, i.e., those having less than about 12-15 carbon atoms. These two patents further state that the higher molecular weight olefinic hydrocarbons are apparently not sufficiently reactive with maleic anhydride to be useful as an alkylating agent, and that higher molecular weight hydrocarbon-substituted succinic acid compounds are almost invariably prepared by reacting maleic anhydride with a halogenated high molecular weight hydrocarbon reactant. Indeed, in U.S. Pat. No. 4,234,435 it is reported that the process as described in these two patents is presently deemed best for preparing the substituted succinic acylating agents.

British Pat. No. 1 492 337 points out that while such acylating agents can be prepared by thermally reacting a polymer having an average molecular weight above about 200 with maleic anhydride at a temperature above 200° C., the reaction rate of such reactions is low and that attempts to improve the reaction rate by increasing the temperature and/or by using superatmospheric pressure results in degradation of maleic anhydride to useless carbon dioxide, water and tarry solids.

U.S. Pat. No. 3,476,774 reports in Example 1 that reaction under nitrogen between polybutene and maleic anhydride conducted in a pressure vessel at 234° C.-236° C. for 6 hours and 40 minutes in o-dichlorobenzene solvent gave an alkenyl succinic anhydride product that had particles of sludge suspended in it. Improvements in yield are reported in Examples 2-4 of the patent wherein a thermal stabilizer (4,4'-methylenebis(2,6-di-tert-butyl-phenol)) was incorporated in the reaction mixture.

U.S. Pat. No. 4,883,886, in discussing the addition reaction between viscous polyalkenes and anhydride reactants such as maleic anhydride, states that a known problem frequently encountered in this reaction is thermal decomposition and polymerization of the unsaturated anhydride reactant at temperatures above about 150° C. According to the patentee, such thermal decomposition is accompanied by evolution of water vapor and oxides of carbon, and in a closed reaction vessel is accompanied by an increase in internal pressure. The patentee continues:

"Under some observed conditions, the thermal decomposition can be so rapid as to be explosive. In the absence of explosive thermal decomposition, a carbon-containing tarry residue is also formed in addition to water vapor and oxides of carbon. * * * Such thermal decomposition and attendant isomerization or polymerization of the unsaturated anhydride reactant has been observed as occurring during its addition reaction with polymeric olefins, e.g., polybutenes and others, in a closed reaction vessel. The carbon-containing residue varies in nature from somewhat granular when the decomposition is only slight to a tarry material mainly adhering to internal surfaces of the reaction vessel when the decomposition is more extensive but well below explosive magnitude. The granular type residue amounts to about from 0.1 to about 0.3 weight percent of the total charge and is generally dispersed in the alkenyl-substituted saturated anhydride addition compound product diluted with unreacted components of the olefin polymer, and is readily separated therefrom by filtration. However, the tarry residue product, which for the most part fouls the internals of the reaction vessel can be as high as 2-3 weight percent of the total charge. The tarry material not adhering to the internal surfaces of the reactor fouls the filter and interferes with filtration of the desired reaction product. Both types of residue are undesirable because of the above noted fouling characteristics and because their formation results in yield reduction of the desired alkenyl-substituted anhydride addition product."

The patentee refers to a number of other patents describing catalysts or agents which decrease such unwanted by-product formation, and utilizes such materials in a particular process in order to suppress the formation of tars and undesired side products.

U.S. Pat. No. 4,152,499 discloses that polybutenes having a higher proportion of terminal double bonds than conventional polybutenes can be produced by polymerizing isobutene with boron trifluoride as the initiator, if (a) the polymerization is carried out at −50° C. to +30° C., (b) from 1 to 20 mmoles of boron trifluoride are used per mole of isobutene, and (c) the mean polymerization time is confined to from 1 to 10 minutes. The patent further discloses that such polybutenes can be reacted with the stoichiometric amount of maleic anhydride, or a slight excess thereof, "in the conventional manner" at from 170° C. to 250° C., and that such polybutenes when heated with maleic anhydride for 4 hours at 200° C. with stirring, followed by removing excess maleic anhydride under greatly reduced pressure exhibited a substantially greater activity than two commercial isobutene polymers. W. German Offenlegungsschrift 29 04 314 teaches the desirability of conducting the polymerization of the isobutene in the same manner except using a polymerization time limited to 1 to 40 seconds, and that to prepare mineral oil additives, "the polyisobutene is reacted in known fashion with the stoichiometric amount or a slight excess of maleic acid anhydride at 170° to 250° C."

It has also been disclosed heretofore that a specified thermal maleinisation reaction can be used to assess the quality (reactivity) of a polybutene polymer. In this procedure polybutene (50 g) is reacted with maleic anhydride (9.8 g), a 1:2 mole ratio, for 24 hours in a stirred reaction tube immersed in a bath of specified hydrocarbons under reflux at 210° C. The reaction is conducted under nitrogen, and the reaction mixture is stirred at a specified number of revolutions per minute. A specifically designed apparatus is suggested for use in this procedure. The procedure results in the formation of both polybutenyl succinic anhydride and a complex resinous co-product formed from maleic anhydride.

As disclosed in our aforesaid prior application, Ser. No. 524,422, it has been found that substantial advantages can be realized by reacting an acidic reactant, such as maleic anhydride, with a substantially aliphatic polymer composed principally or entirely of polyisobutene in a mole ratio of acidic reactant(s): polymer is at least 1:1, provided that at least 50% (preferably at least 75%) of the polyisobutene content of such polymer has an end group represented by the formula

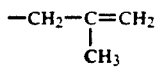

and the reaction mixture is maintained under superatmospheric pressure during at least a substantial portion of the reaction period. Most preferably, the polymer consists essentially of polyisobutene (i.e., it contains at least 50 mole % and more preferably at least 60 mole % of polymerized isobutene) and at least 50% (more desirably at least 75%) of the total polymer(s) is polyisobutene having such end group.

THE INVENTION

This invention provides in one of its embodiments novel and eminently useful ashless dispersants prepared by use of the substituted acylating agents formed as described in our aforesaid prior application Ser. No. 524,422. More particularly, the so-formed polybutenyl succinic acids or acid derivatives thereof (polybutenyl succinic anhydrides, polybutenyl succinic acid halides, polybutenyl succinic acid lower alkyl esters) are especially useful in the manufacture of polybutenyl succinic acid esters, polybutenyl succinimides or succinamides, and polybutenyl succinic ester-amides by reaction with alcohols or amines, or combinations thereof. The amines are preferably alkylene polyamines such as ethylene or propylene diamines, diethylene triamine, triethylene tetramine, tetraethylene pentamine, pentaethylene hexamine, etc. The alcohols are preferably polyhydric alcohols. Such polybutenyl succinic acid esters, polybutenyl succinimides, polybutenyl succinamides, and polybutenyl succinic ester-amides are especially useful as ashless dispersants in lubricating oils and functional fluids.

Accordingly, one embodiment of this invention provides a carboxylic derivative composition produced by reacting at least one substituted succinic acylating agent with a reactant selected from the group consisting of (1) at least one amine having at least one primary or secondary amino group, (2) at least one alcohol, and (3) a combination of at least one amine having at least one primary or secondary amino group and at least one alcohol, the components of (3) being reacted with said at least one substituted succinic acylating agent concurrently or sequentially in any order, said at least one succinic acylating agent being prepared by reacting (i) at least one substantially aliphatic polymer of at least one lower olefin, and (ii) an acidic reactant or a mixture of two or more acidic reactants represented by the general formula

wherein R and R' are independently —OH, —O—lower alkyl, a halogen atom, or taken together are a single oxygen atom; the process of preparing said at least one succinic acylating agent being characterized in that:

a) the substantially aliphatic polymer is comprised predominantly or entirely of polyisobutene, at least 50% of the polyisobutene content of such polymer having an end group represented by the formula

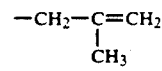

b) the mole ratio of said acidic reactant(s): said polymer(s) is at least 1:1; and c) the reaction mixture is maintained under superatmospheric pressure during at least a substantial portion of the reaction period.

Generally speaking, the carboxylic derivative compositions of this invention are formed from acylating agents having an average total tar rating as determined by the method described in the specification hereof that is at least 25% lower than the average total tar rating of a corresponding acylating agent made in the same way under the same reaction conditions using a polyisobutene containing up to 10% of the above-depicted end group. Preferred acylating agents used in forming the carboxylic derivative compositions of this invention are characterized by having an average total tar rating as determined by the method described in the specification hereof that is at least about 40% lower (for example about 43% lower) and most preferably at least 50% lower than the average total tar rating of a corresponding product made in the same way under the same reaction conditions using a polyisobutene containing less than 10% of the above-depicted end group. In this connection it will be appreciated that such terms as "total tars value", "average total tars", "total tar content" and "total tars" are alternative ways of referring to the average total tar rating, since all such terms or expressions refer to the numerical result obtained by use of the method described in the specification hereof.

Particularly preferred acylating agents of the types described above have a succination ratio of less than 1.3—i.e., the acylating agents have within their structure an average of less than 1.3 succinic groups per each substituent group derived from the aforesaid substantially aliphatic polymer.

Another embodiment of this invention involves the process of forming a carboxylic derivative composition which comprises reacting at least one substituted succinic acylating agent with a reactant selected from the group consisting of (1) at least one amine having at least one primary or secondary amino group, (2) at least one alcohol, and (3) a combination of at least one amine having at least one primary or secondary amino group and at least one alcohol, the components of (3) being reacted with said at least one substituted succinic acylating agent concurrently or sequentially in any order, said at least one succinic acylating agent having been prepared by reacting (i) at least one substantially aliphatic polymer of at least one lower olefin, and (ii) an acidic reactant or a mixture of two or more acidic reactants represented by the general formula

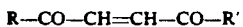

R—CO—CH=CH—CO—R' wherein R and R' are independently —OH, —O— lower alkyl, a halogen atom, or taken together are a single oxygen atom; the process of preparing said acylating agent being characterized in that:
a) the substantially aliphatic polymer is comprised predominantly or entirely of polyisobutene, at least 50% of the polyisobutene content of such polymer having an end group represented by the formula

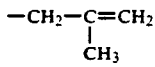

$$-CH_2-C=CH_2$$
$$\quad\quad |$$
$$\quad\quad CH_3$$

b) the mole ratio of said acidic reactant(s): said polymer(s) is at least 1:1; and
c) the reaction mixture is maintained under superatmospheric pressure during at least a substantial portion of the reaction period.

The preferred acylating agents of this type for use in the process are characterized by having an average total tar rating as determined by the method described in the specification hereof that is at least about 40% lower (for example about 43% lower) and most preferably at least 50% lower than the average total tar rating of a corresponding product made in the same way under the same reaction conditions using a polyisobutene containing less than 10% of the above-depicted end group. Particularly preferred acylating agents of this type have a succination ratio of less than 1.3.

A further embodiment of this invention relates to a two-stage process for the production of a carboxylic derivative composition and to the novel products formed thereby. Pursuant to this embodiment, a carboxylic derivative composition is produced by a process which comprises:

A. reacting (i) at least one substantially aliphatic polymer of at least one lower olefin, and (ii) an acidic reactant or a mixture of two or more acidic reactants represented by the general formula

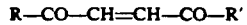

R—CO—CH=CH—CO—R' wherein R and R' are independently —OH, —O— lower alkyl, a halogen atom, or taken together are a single oxygen atom; the process of preparing said acylating agent being characterized in that a) the substantially aliphatic polymer is comprised predominantly or entirely of polyisobutene, at least 50% of the polyisobutene content of such polymer having an end group represented by the formula

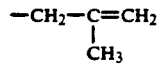

$$-CH_2-C=CH_2$$
$$\quad\quad |$$
$$\quad\quad CH_3$$

b) the mole ratio of said acidic reactant(s): said polymer(s) is at least 1:1; and c) the reaction mixture is maintained under superatmospheric pressure during at least a substantial portion of the reaction period, whereby a substituted succinic derivative composition is formed; and B. reacting said substituted succinic acylating agent with a reactant selected from the group consisting of (1) at least one amine having at least one primary or secondary amino group, (2) at least one alcohol, and (3) a combination of at least one amine having at least one primary or secondary amino group and at least one alcohol, the components of (3) being reacted with said at least one substituted succinic acylating agent concurrently or sequentially in any order.

Pursuant to a preferred embodiment of this two-stage process, the substituted succinic derivative composition formed in Stage A and used in Stage B has an average total tar rating as determined by the method described in the specification hereof that is at least about 40% lower (for example about 43% lower) and most preferably at least 50% lower than the average total tar rating of a corresponding product made in the same way under the same reaction conditions using a polyisobutene containing less than 10% of the above-depicted end group. Particularly preferred acylating agents of this type have a succination ratio of less than 1.3.

The carboxylic derivative compositions of this invention formed as described above have a good balance of oxidative and thermal stability, and thus can be subjected to more stringent thermooxidative conditions than corresponding products made in the same way under the same reaction conditions using a polyisobutene containing less than 10% of the above-depicted end group.

Also provided by this invention are carboxylic derivative compositions produced as above which are further reacted with one or more post-treating reactants such as the following: an inorganic phosphorus acid or anhydride; a water-hydrolyzable organic phosphorus compound and water; an organic phosphorus compound; phosphorus pentasulfide; a boron compound; a mono- or polycarboxylic acid, anhydride or acid halide; a mono- or polyepoxide or thioepoxide; an aldehyde or ketone; carbon disulfide; glycidol; urea, thiourea or guanidine; an organic sulfonic acid; an alkenyl cyanide; diketene; a diisocyanate; an alkane sultone; a 1,3-dicarbonyl compound; a sulfate of an alkoxylated alcohol or alkoxylated phenol; a cyclic lactone; a cyclic carbonate or thiocarbonate, a linear monocarbonate or polycarbonate, or chloroformate; a nitrogen-containing carboxylic acid; a hydroxy-protected chlorodicarbonyloxy compound, a lactam, thiolactam, thiolactone or dithiolactone; a cyclic carbamate, cyclic thiocarbamate or cyclic dithiocarbamate; a hydroxyaliphatic carboxylic acid; an oxidizing agent; the combination of phosphorus pentasulfide and a polyalkylene polyamine; the combination of a carboxylic acid or an aldehyde or ketone and sulfur or sulfur chloride; the combination of an aldehyde and a phenol; the combination of an aldehyde and an O,O-diester of dithiophosphoric acid; the combination of a hydroxyaliphatic carboxylic acid and a boric acid; the combination of a hydroxyaliphatic acid, then formaldehyde and a phenol; the combination of a hydroxyaliphatic acid and then a dicarboxylic acid; the combination of formaldehyde and a phenol, and then glycolic acid; the combination of a hydroxyaliphatic carboxylic acid or oxalic acid and then a diisocyanate; the combination of an inorganic acid or anhydride of phosphorus or a partial or total sulfur analog thereof and a boron compound; the combination of an organic diacid, then an unsaturated fatty acid, and then a nitroso-aromatic amine, optionally followed by a boron compound and optionally followed by glycolic acid; the combination of an aldehyde and a triazole; the combination of an aldehyde and a triazole, then a boron compound; and the combination of cyclic lactone and a boron compound. The fact that such a vast array of post-treating agents can be used does not signify that they are equivalent to each other in every instance. For example, some of the foregoing post-treating agents improve the antiwear properties of the succinimide, succinic ester, and/or succinic ester-amide with which they are reacted. Examples are the inorganic phosphoric acids or anhydrides, and the water-hydrolyzable organic phosphorus compounds and water, when used in combination (concurrently or sequentially) with a boron compound. Other post-treating agents have no appreciable effect on antiwear performance but are effective in improving other properties such as passivity toward polymeric materials used in fabricating seals, diaphragms, and other components with which oils of lubricating viscosity frequently come in contact during actual service conditions.

Still further embodiments of this invention relate to the provision of novel and eminently useful compositions wherein the carboxylic derivative compositions of this invention whether or not post-treated as above, are utilized in combination with one or more other components, especially zinc hydrocarbyl dithiophosphates, Group I or II metal detergent compositions, active sulfur-containing antiwear and/or extreme pressure agents, and/or metal-free phosphorus-containing antiwear and/or extreme pressure agents.

These and other embodiments, features and advantages of this invention will be apparent from the ensuing description and appended claims. For the sake of brevity, in various p1 ces throughout the ensuing disclosure reference is n. ..e to a number of patents, published patent applications, and journal articles. The disclosures of all such documents are expressly incorporated herein in toto by reference.

Succinic Acylating Agents

As noted above, the succinic acylating agents utilized in forming the carboxylic acid derivative compositions of this invention are formed by reacting (i) at least one substantially aliphatic polymer of at least one lower olefin, and (ii) an acidic reactant or a mixture of two or more acidic reactants represented by the general formula $$R-CO-CH=CH-CO-R' \quad (I)$$

wherein R and R' are independently —OH, —O— lower alkyl, a halogen atom, or taken together are a single oxygen atom. This process is characterized in that a) the substantially aliphatic polymer is comprised predominantly or entirely of polyisobutene, at least 50% of the polyisobutene content of such polymer having an end group represented by the formula

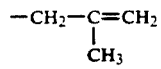

b) the mole ratio of said acidic reactant(s): said polymer(s) is at least 1:1; and c) the reaction mixture is maintained under superatmospheric pressure during at least a substantial portion of the reaction period.

In order to determine in any given polyisobutene the proportion thereof that contains the above identified end group, use can be made of Infra-Red Spectroscopy and, more preferably, $C_{13}$ Nuclear Magnetic Resonance. In $C_{13}$ NMR, typical olefin chemical shifts appear between 100 and 160 ppm. Structural identification can be confirmed by comparison with $C_{13}$ spectra of known olefins. See for example, *Atlas of Carbon-13 NMR Data*, edited by E. Breitmaier, G. Haas and W. Voelter, Spectra numbers 30–107. Quantitation can be accomplished by suppression of the NOE produced by proton attachment to carbon. Sufficient delay time is allowed for complete carbon relaxation.

Preferred acidic reactants represented by Formula (I) above include such compounds as maleic acid, fumaric acid, the lower alkyl ($C_{1-7}$) esters of such acids, the acid halides (preferably the acid fluorides or chlorides) of such acids, maleic anhydride, or mixtures of any two or more of any such compounds. Other similar compounds which can be used are itaconic acid, itaconic anhydride, citraconic acid, citraconic anhydride, mesaconic acid, the lower alkyl esters and the acid halides of such acids, and the like. Maleic anhydride is the most preferred reactant for use in the process.

Preferably, the entire reaction or substantially the entire reaction is conducted under superatmospheric pressure, such as by conducting the entire reaction or substantially the entire reaction in a closed reaction system at superatmospheric pressure. Most preferably, the process is conducted such that the superatmospheric pressure on the reaction mixture decreases after passing through an initial peak pressure, and then increases to another elevated pressure, especially where the latter elevated pressure is higher than the initial peak pressure.

For best results, (a) at least a substantial portion of the reaction is conducted at a pressure in the range of about 1 to about 75 psig or more (and preferably in the range of about 4 to about 50 psig), (b) the temperature of the reaction mixture is maintained in the range of about 200° to about 265° C. and more preferably in the range of about 220° to about 265° C. throughout substantially the entire reaction period, and (c) the mole ratio of the acidic reactant(s): the polymer(s) is in the range of 1.1:1 to about 3:1, and preferably in the range of 1.1:1 to 1.9:1. It is to be understood however that departures from the foregoing ranges of pressure, temperature and/or proportions may be utilized in any given situation where such departure is deemed desirable under the given circumstances involved. All that is required in the practice of this invention is that the reaction be conducted under reaction conditions, including super-atmospheric pressure, that enable the reaction to proceed without encountering excessive decomposition or excessive by-product formation (e.g., excessive tar or polymer formation).

It is particularly preferred to employ the reactants in mole ratios of acidic reactant to polyisobutene such that the product contains an average molar ratio of succinic groups to polyisobutene chains below 1.3:1. In other words, the succination ratio of the acylating agent (excluding unreacted components) is less than 1.3.

The reaction rate in this process is high, the yields of desired product are high, and despite the fact that superatmospheric pressures and substantially elevated temperatures are used, the process forms only small amounts of tars or resinous co-products, even when employing as much as a 20% or more molar excess of maleic anhydride. Indeed, any unreacted acidic reactant such as maleic anhydride, maleic acid, fumaric acid, or the like can be, and preferably is, recovered from the reaction mixture, and thus is available for use either as recycle to the process or for other uses. Moreover, inasmuch as chlorine is not used in the process, the expense and difficulties associated with handling chlorine on a plant scale are eliminated, and the product is less corrosive than corresponding products formed by use of chlorine.

Another advantage of this process is that thermal stabilizers or other additive materials to reduce tar formation are not required. Indeed, many of the known materials to reduce tar formation are halogen-containing substances (see for example U.S. Pat. Nos. 3,927,041; 3,935,249; 3,953,475; 3,954,812; 3,960,900; 3,985,672; 4,008,168; 4,086,251; 4,414,397; 4,434,071; and 4,496,746). Halogen-containing components are generally undesirable because they tend to leave halogen-containing residues in the product.

Thus products with almost no tarry co-products or halogen-containing residues can be formed in exceptionally high yields in the foregoing process without use of such extraneous materials as thermal stabilizers and tar suppressors which add to the cost of the operation and can leave undesirable impurities in the product. In fact, it has been found possible to achieve higher conversions of maleic anhydride to alkenyl succinic anhydride by use of the process of this invention without a thermal stabilizer than the conversions reported in U.S. Pat. No. 3,476,774 (Examples 2-4) wherein a thermal stabilizer was used. For example, the yields based on conversion of maleic anhydride to the desired product reported in Examples 2-4 of the patent average 80%. In contrast, a group of 8 runs pursuant to the process conducted as in Examples 6-8 presented hereinafter gave a conversion on the same basis averaging 92%.

The polybutenes or like polymers utilized in this process may have number average molecular weights in the range of 500 to 100,000 or more. The preferred polymers are those having number average molecular weights in the range of 700 to 5,000, and the most preferred polymers are those having number average molecular weights in the range of 800 to 1,300.

Methods for producing polybutenes useful in the practice of this process are described in U.S. Pat. No. 4,152,499 and in W. German Offenlegungsschrift 29 04 314, the disclosures of which are incorporated herein by reference. Suitable products are understood to be available under the trade designation "Ultravis".

If desired, the reaction can be conducted in an inert liquid reaction medium or diluent such as one or more saturated aliphatic, saturated cycloaliphatic, or aromatic hydrocarbons, e.g. mineral oil, etc. Preferably, however, the reaction is conducted in the absence of an ancillary reaction solvent or diluent. A small amount of catalyst such as aluminum trichloroide, triethylaluminum, methylaluminum sesquichloride, diethylaluminum chloride, or the like, may be employed in the process.

The following examples illustrate the production of the succinic acylating agents used in the practice of this invention. In these examples all parts and percentages are by weight unless otherwise specified. Also the "cook period" referred to in the examples is designated as the point where the reaction mass reaches its specified reaction temperature, and thus at this point the cook time is equal to 0. The polybutene used in Examples 1-6 was a substantially pure polyisobutylene with a number average molecular weight of about 995. Approximately 78% of the polymer had an end group as depicted in Formula I above. In Examples 6-8 the polybutene employed was a substantially pure polyisobutylene with a number average molecular weight of about 1,300. This polybutene also contained about 78% of polymer having the above-depicted end group. Conventional commercially-available polyisobutene contains less than about 10% of polymer containing such end group.

EXAMPLE 1

Into an autoclave were charged 1200 parts of polybutene (PIB), 130.7 parts of maleic anhydride (MA) and 0.12 part of aluminum trichloride. The mole ratio of MA:PIB was thus 1:1. A vacuum (−26 inches of mercury) was applied to the autoclave for 10 minutes to remove the oxygen (air), and while holding the system under a low vacuum the autoclave was heated. When the autoclave temperature reached 90° C., the agitator was turned on. When the temperature reached 225° C., the pressure within the autoclave was 12.5 psig. Thereupon the reaction mixture was kept at 225° C. for 5 hours while continuously agitating the reaction mixture. The pressure profile on the reaction mass during this period was as follows:

| Cook Time, minutes | Pressure, psig |
| --- | --- |
| 0 | 12.5 |
| 5 | 13.0 |
| 15 | 8.0 |
| 25 | 5.0 |
| 40 | 4.5 |
| 50 | 3.5 |
| 65 | 2.0 |
| 80 | 1.0 |
| 95 | 0.5 |
| 135 | 0 |
| 150 | −0.5 |
| 170 | 0 |
| 185 | 0.5 |
| 210 | 1.5 |
| 235 | 3.0 |
| 255 | 4.0 |
| 300 | 6.0 |

The resultant reaction product was subjected to vacuum stripping to remove volatiles (primarily unreacted maleic anhydride). The polybutenyl succinic anhydride reaction product had an acid number before stripping of 0.92, and an acid number after stripping of 0.76.

EXAMPLE 2

The general procedure of Example 1 was repeated, the chief difference being that the reactants were kept at 240° C. during the major portion of the reaction period. The pressure profile on the reaction mass during the reaction was as follows:

| Cook Time, minutes | Pressure, psig |
|---|---|
| 0 | 17.0 |
| 5 | 14.0 |
| 25 | 6.0 |
| 35 | 4.5 |
| 45 | 3.0 |
| 55 | 2.5 |
| 75 | 2.0 |
| 90 | 2.0 |
| 105 | 2.0 |
| 135 | 3.5 |
| 170 | 5.0 |
| 205 | 5.0 |
| 250 | 6.0 |
| 300 | 7.0 |

The resultant reaction product was subjected to vacuum stripping to remove volatiles (primarily unreacted maleic anhydride). The polybutenyl succinic anhydride reaction product had an acid number before stripping of 0.92, and an acid number after stripping of 0.82.

EXAMPLE 3

Using the same reactants and the same general procedure as in Example 1, the reactants were employed in a MA:PIB mole ratio of 1.1:1 (143.8 parts of MA and 1200 parts of PIB). The pressure profile on the reaction mass during the reaction at 225° C. was as follows:

| Cook Time, minutes | Pressure, psig |
|---|---|
| 0 | 12.0 |
| 5 | 14.5 |
| 10 | 12.0 |
| 30 | 6.0 |
| 60 | 3.5 |
| 90 | 2.0 |
| 120 | 1.0 |
| 150 | 1.0 |
| 180 | 1.0 |
| 210 | 1.0 |
| 240 | 1.5 |
| 270 | 3.0 |
| 300 | 4.5 |

The polybutenyl succinic anhydride reaction product had an acid number before vacuum stripping of 1.04, and an acid number after stripping of 0.81.

EXAMPLE 4

In this run the same reactants as in Example 1 were reacted at 240° C. at a mole ratio (MA:PIB) of 1.1:1. The pressure profile on the reaction mass during the reaction was as follows:

| Cook Time, minutes | Pressure, psig |
|---|---|
| 0 | 17.0 |
| 10 | 15.0 |
| 25 | 10.0 |
| 30 | 9.0 |
| 45 | 7.5 |
| 55 | 7.0 |
| 65 | 6.0 |
| 80 | 5.5 |
| 95 | 6.0 |
| 115 | 6.0 |
| 135 | 8.5 |
| 155 | 10.0 |
| 180 | 13.5 |
| 195 | 16.0 |
| 215 | 19.0 |
| 235 | 22.5 |
| 250 | 25.5 |
| 265 | 28.0 |
| 280 | 31.5 |
| 300 | 34.0 |

The acid number of the polybutenyl succinic anhydride reaction product before vacuum stripping was 1.02. After stripping the product had an acid number of 0.91.

EXAMPLE 5

The same reactants as in Example 1 were reacted at 240° C. at a mole ratio (MA:PIB) of 1.2:1 (155.65 parts of MA and 1190 parts of PIB). The pressure profile on the reaction mass during the reaction was as follows:

| Cook Time, minutes | Pressure, psig |
|---|---|
| 0 | 18.0 |
| 5 | 17.5 |
| 35 | 7.0 |
| 60 | 5.0 |
| 90 | 4.5 |
| 120 | 5.0 |
| 150 | 6.0 |
| 180 | 7.0 |
| 210 | 10.0 |
| 240 | 13.5 |
| 270 | 17.0 |
| 300 | 21.0 |

The acid numbers of the polybutenyl succinic anhydride reaction product were 1.09 before stripping, and 0.95 after stripping.

EXAMPLE 6

Into an autoclave were charged 1211.8 parts of polybutene (PIB), 118.9 parts of maleic anhydride (MA) and 0.12 part of aluminum trichloride. The mole ratio of MA:PIB was thus 1.3:1. A vacuum (−26 inches of water) was applied to the autoclave for 10 minutes to remove the oxygen (air), and while holding the system under a low vacuum the autoclave was heated. When the autoclave temperature reached 105° C., the agitator was turned on. When the temperature reached 240° C., the pressure within the autoclave was 17.0 psig. Thereupon the reaction mixture was kept at 240° C. for 5 hours while continuously agitating the reaction mixture. The pressure profile on the reaction mass during this period was as follows:

| Cook Time, minutes | Pressure, psig |
|---|---|
| 0 | 17.0 |
| 15 | 14.0 |
| 30 | 10.5 |
| 45 | 8.0 |
| 70 | 6.5 |
| 95 | 6.5 |
| 115 | 8.0 |
| 150 | 12.0 |
| 195 | 19.0 |
| 230 | 26.0 |
| 260 | 33.0 |
| 300 | 40.5 |

The reaction product was subjected to vacuum stripping to remove volatiles (primarily unreacted maleic anhydride). The acid numbers of the polybutenyl succinic anhydride reaction product were 0.84 before stripping, and 0.78 after stripping.

EXAMPLE 7

The same reactants as in Example 6 were reacted in the same general manner at 240° C. at a mole ratio (MA:PIB) of 1.5:1 (135.3 parts of MA and 1195.4 parts of PIB). The pressure profile on the reaction mass during the reaction was as follows:

| Cook Time, minutes | Pressure, psig |
| --- | --- |
| 0 | 15.5 |
| 5 | 16.0 |
| 20 | 12.5 |
| 40 | 10.0 |
| 45 | 9.5 |
| 60 | 8.5 |
| 80 | 8.5 |
| 110 | 10.0 |
| 140 | 14.0 |
| 180 | 20.5 |
| 205 | 26.5 |
| 245 | 37.0 |
| 255 | 40.5 |
| 270 | 43.0 |
| 300 | 50.0 |

The acid numbers of the polybutenyl succinic anhydride reaction product were 0.91 before stripping, and 0.83 after stripping.

Table 1 summarizes the total tar content and the stripped acid number (i.e., the acid number of the residual product after stripping) of the respective products of Examples 1-5, and provides a comparison of the corresponding values on a product made under the same general reaction conditions (including superatmospheric pressure) using a PIB that contained less than 10% of the above-depicted end group, and wherein the mole ratio (MA:PIB) was 1:1.

The procedure for determination of total tar content used herein is as follows: After completion of the reaction run, the reactor head and attached agitator are removed, and the reactor contents are transferred from the autoclave to storage and analysis bottles. The appearance of the reactor and its component parts is immediately rated by at least two, and preferably three, trained technical personnel. The rating takes place in a specific manner, namely:

1) Each of the three major internal components of the autoclave—i.e., the sides, the bottom, and the agitator, is independently rated.

2) The rating is based upon the visual appearance of the component and the amount of tar present. The rating scale ranges from 1 to 10, with "1" representing a perfectly clean component showing no evidence of tar formation. The rating of "10" represents a heavily tarred component which is completely covered with tar. In general, an intermediate rating corresponds to the area of the surface covered by the black tar. For example, a rating of "7" means that approximately 70% of the surface is covered with tar.

3) Each person making the evaluations works independently of the other person(s) and thus records his/her observations without consultation with, or knowledge of the ratings made by, the other person(s).

4) The rating numbers for the three individual components are added together for each individual evaluator and the sum of all of these totals are averaged (i.e., divided by the number of evaluators) to yield an average total tar rating reported herein.

5) The average total tar rating scale is as follows:
3 to 5—Excellent; very clean reactor, tar formation minimal or non-existent
6 to 10—Good; some tar formation
11 to 14—Fair; significant level of tar formation
15 to 20—Poor; medium to heavy tar formation
20 to 30—Very Poor; heavy to severe tar formation

TABLE 1

Key Properties of Polyisobutenyl Succinic Anhydrides

| Example | Reaction Temperature | MA:PIB Ratio | Maximum Pressure | Total Tars | Stripped Acid No. |
| --- | --- | --- | --- | --- | --- |
| 1 | 225° C. | 1.00 | 13.0 psig | 4 | 0.76 |
| 2 | 240° C. | 1.00 | 17.0 psig | 4 | 0.82 |
| 3 | 225° C. | 1.10 | 14.5 psig | 3 | 0.81 |
| 4 | 240° C. | 1.10 | 34.0 psig | 3 | 0.90 |
| 5 | 240° C. | 1.20 | 21.0 psig | 3 | 0.95 |
| Control | 225° C. | 1.00 | 15.0 psig | 7 | 0.60 |

EXAMPLE 8

The same reactants as in Example 6 were reacted in the same general manner at 240° C. at a mole ratio (MA:PIB) of 1.3:1 (118.9 parts of MA and 1211.8 parts of PIB) except that the aluminum chloride catalyst was not used. Agitation of the reactants was commenced when the temperature reached 60° C. The pressure profile on the reaction mass during the reaction was as follows:

| Cook Time, minutes | Pressure, psig |
| --- | --- |
| 0 | 16.5 |
| 10 | 11.5 |
| 35 | 7.0 |
| 50 | 6.0 |
| 75 | 6.0 |
| 100 | 7.0 |
| 130 | 9.0 |
| 165 | 11.5 |
| 195 | 14.5 |
| 240 | 20.0 |
| 260 | 22.0 |
| 280 | 25.0 |
| 300 | 27.0 |

The acid number of the polybutenyl succinic anhydride reaction product before stripping was 0.84, and after stripping, 0.77. Average total tars was 4.

EXAMPLE 9

This example demonstrates that unreacted maleic anhydride can be recovered from the reaction mixture and recycled for use in subsequent runs. In particular, an initial batch run was made followed by two recycle batch runs in which the maleic anhydride from the prior run was used as part of the total maleic anhydride charge. In this series of runs the same reactants as in Example 6 were used. The charges to the reactor were:
Run 1—MA, 118.9 parts; PIB, 1211.8 parts; AlCl$_3$, 0.12 part.
Run 2—Fresh MA, 107.6 parts, recycled MA, 11.7 parts; PIB, 1211.8 parts; AlCl$_3$, 0.12 part.
Run 3—Fresh MA, 106.4 parts, recycled MA, 12.5 parts; PIB, 1211.8 parts; AlCl$_3$, 0.12 part.
Agitation of the reactants was commenced when the temperature reached 60°-70° C. The pressure profile on the reaction mass during the reaction was as follows:

| Run 1 | | Run 2 | | Run 3 | |
|---|---|---|---|---|---|
| Cook Time minutes | Pressure psig | Cook Time minutes | Pressure psig | Cook Time minutes | Pressure psig |
| 0 | 19.0 | 0 | 20.0 | 0 | 16.0 |
| 10 | 14.5 | 10 | 16.0 | 10 | 14.0 |
| 25 | 9.5 | 25 | 9.0 | 20 | 9.5 |
| 35 | 8.0 | 40 | 7.5 | 40 | 7.0 |
| 60 | 5.5 | 65 | 5.0 | 55 | 5.0 |
| 95 | 5.5 | 85 | 5.0 | 85 | 5.0 |
| 130 | 7.5 | 120 | 6.0 | 100 | 5.0 |
| 150 | 9.0 | 155 | 9.0 | 120 | 5.0 |
| 180 | 12.0 | 175 | 11.5 | 170 | 9.0 |
| 225 | 19.0 | 215 | 17.0 | 200 | 11.0 |
| 255 | 23.0 | 240 | 21.0 | 230 | 16.0 |
| 260 | 28.0 | 260 | 23.5 | 285 | 23.5 |
| 300 | 30.0 | 280 | 27.0 | 300 | 25.0 |
| | | 300 | 30.0 | | |

Table 2 includes a summary of the results of this series of runs.

TABLE 2

| | Highlights of Recycle Process | | | |
|---|---|---|---|---|
| Run No. | % MA Recycled | Total Tars | Stripped Acid No. | Unreacted PIB, % |
| 1 | None | 3 | 0.75 | 27.2 |
| 2 | 9.8 | 3 | 0.73 | 24.0 |
| 3 | 10.5 | 3 | 0.73 | 24.2 |

EXAMPLE 10

The procedure of Example 4 was repeated yielding the following pressure profile:

| Cook Time, minutes | Pressure, psig |
|---|---|
| 0 | 17.0 |
| 10 | 15.0 |
| 25 | 10.0 |
| 30 | 9.0 |
| 45 | 7.5 |
| 55 | 7.0 |
| 65 | 6.0 |
| 80 | 5.5 |
| 95 | 6.0 |
| 115 | 6.0 |
| 135 | 8.5 |
| 155 | 10.0 |
| 180 | 13.5 |
| 195 | 16.0 |
| 215 | 19.0 |
| 235 | 22.5 |
| 250 | 25.5 |
| 265 | 28.0 |
| 280 | 31.5 |
| 300 | 34.0 |

The reaction mixture before stripping had a total tar content of 3. The acid number of the polybutenyl succinic anhydride product after vacuum stripping was 0.91.

The reaction product mixtures formed in the above process are of particular advantage in that they contain little or no tars; the materials used in Examples 1-10 usually gave a rating by the above procedure of 3 or 4. Thus the interior surfaces of the reactor were free or essentially free of tars or other resinous coatings, and moreover the effective utilization of the raw materials used in the process was high. Moreover, after removal of residual unreacted acidic reactant (i.e., the maleic anhydride or like carboxylic reactant) charged to the reactor (if any remains unreacted) such as by distillation or stripping at reduced pressure, the remainder of the product generally will have an acid number of at least 0.7, preferably at least 0.8, and in the most preferred cases, at least 0.9. Such product can be used without further treatment or purification either as an additive or as a raw material for use in the production of the dispersant additives of this invention.

As shown by data presented in Table 1 hereinabove, the average total tar rating of the PIBSA made in Example 1 was 43% lower than the average total tar rating of the PIBSA made in the same way under essentially the same reaction conditions using a polyisobutene containing less than 10% of the end group depicted hereinabove.

More recent experimental work along these lines provided additional confirmation of this advantageous result. For example, two runs (Examples 11 and 12) were conducted generally as in Example 4 using a polyisobutene from a different supplier that had a number average molecular weight (by GPC) of 1323 and that contained approximately 73% of polymer having the end group depicted hereinabove (as indicated by the supplier). A control run was conducted in the same manner using a polyisobutene having a number average molecular weight of 1314 (by GPC) but which contained at most only 15% of polymer with such end group. In each such run the reaction was conducted for 5 hours at 240° C. utilizing a 1.10 molar ratio of maleic anhydride to polyisobutene. Table 3 summarizes the results obtained, including the average total tar ratings on the products.

TABLE 3

| | Results of Comparative Runs | | | | |
|---|---|---|---|---|---|
| Example | Maximum Pressure | Total Tars | Unstripped Acid No. | Stripped Acid No. | Unreacted PIB, % |
| 11 | 13.8 psig | 9.0 | 0.73 | 0.66 | 25.4 |
| 12 | 21.0 psig | 9.7 | 0.73 | 0.64 | 23.3 |
| Control | 17.0 psig | 19.0 | 0.70 | 0.53 | 40.3 |

From Table 3 it can be seen that the average total tar rating of the PIBSA made in Examples 11 and 12 averaged about 51% less than the average total tar rating of the PIBSA made in the control run.

Typically the difference in acid number of the reaction product before and after removal of residual acidic reactant(s) therefrom is no greater than 0.23, preferably no greater than 0.16, and most preferably is 0.10 or less.

As noted above, the polyolefin, most preferably polyisobutene, of the succinic acylating agent has a number average molecular weight of at least 500, and preferably has a number average molecular weight in the range of 700 to 5,000, and more preferably in the range of 800 to 2,500, and especially 800 to 1,300. In this connection, the reputable commercial manufacturers of such polyolefins identify their products, inter alia, by means of number average molecular weights, and the designations provided by such suppliers can be relied upon. In any instance where it is desired to make an independent determination of number average molecular weight of the polybutene being used, recourse may be had to the procedures described hereinafter.

The polybutenyl succinic acids or acid derivatives thereof (polybutenyl succinic anhydrides, polybutenyl succinic acid halides, polybutenyl succinic acid lower alkyl esters) prepared as above are useful as corrosion inhibitors for liquid fuels such as gasoline and middle distillate fuels (diesel fuel, burner fuel, turbine fuel, jet fuel, kerosene, etc.).

Suitable procedures which can be used in order to make an independent determination of the number average molecular weight ($\overline{M}n$) of the polyalkene from which the alkenyl substituent of the acylating agent is derived involve use of either of two methods, namely, vapor pressure osmometry (VPO) or gel permeation chromatography (GPC). The VPO determination should be conducted in accordance with ASTM D-2503-82 using high purity toluene as the measuring solvent.

Alternatively, a GPC procedure can be employed. As is well known, the GPC technique involves separating molecules according to their size in solution. For this purpose liquid chromatographic columns are packed with a styrene-divinyl benzene copolymer of controlled particle and pore sizes. When the polyalkene molecules from which the substituent is derived are transported through the GPC columns by a solvent (tetrahydrofuran), the polyalkene molecules small enough to penetrate into the pores of the column packing are retarded in their progress through the columns. On the other hand, the polyalkene molecules which are larger either penetrate the pores only slightly or are totally excluded from the pores. As a consequence, these larger polyalkene molecules are retarded in their progress through the columns to a lesser extent. Thus a velocity separation occurs according to the size of the respective polyalkene molecules. In order to define the relationship between polyalkene molecular weight and elution time, the GPC system to be used is calibrated using known molecular weight polyalkene standards and an internal standard method. Details concerning such GPC procedures and methods for column calibration are extensively reported in the literature. See for example, W. W. Yau, J. J. Kirkland, and D. D. Bly, *Modern Size-Exclusion Liquid Chromatography*, John Wiley & Sons, 1979, Chapter 9 (pages 285-341), and references cited therein.

For present purposes, the sample of polyalkene to be subjected to GPC analysis is injected into a high purity tetrahydrofuran mobile phase flowing at 1.00 mL/min. Such sample is separated by elution through a set of GPC columns arranged in series and containing seriatim 1000, 500, 100, and 50 Angstrom pore sized styrene-divinyl benzene beads of 5 micron gel size. An internal standard, flowers of sulfur, is used with the sample to insure proper elution flow rate. The polyalkene eluate is detected by a differential refractive index detector. The signal from this detector as a function of time is digitized and stored by a data system. After the chromatograph is completed the stored data is processed to generate the $\overline{M}n$ of the polyalkene.

In general, the $\overline{M}n$ determined by the VPO and GPC methods should agree within the precision of the respective methods.

When it is desired to determine the succination ratio of any given succinic acylating agent, the number average molecular weight of the aliphatic polymer comprised predominantly or entirely of polyisobutene is determined by the above procedure. Then the total weight of the substituent groups present in the substituted succinic acylating agent is determined by conventional methods for determination of the number of carbonyl functions. The preferred procedure for use involves nonaqueous titration of the substituted acylating agent with standardized sodium isopropoxide. In this procedure the titration is conducted in a 1:1 mineral spirits:1-butanol solvent system. An alternative, albeit less preferred, procedure is the ASTM D-94 procedure.

The results from the procedure just described and the number average molecular weight determinations are used in calculating the weight of substituent groups per unit weight of total sample.

It is to be noted that in determining the succination ratio of the alkenyl succinic acylating agent, the determination is to be based on the active portion of the sample. That is to say, alkenyl succinic acylating agents can be and are often produced as a mixture with an inactive component or diluent such as unreacted polyisobutene and/or process oil. Thus for the purpose of succination ratio determination, such inactive component or diluent should not be considered a part of the succinic acylating agent. Accordingly, a separation as between the inactive component or diluent and the alkenyl succinic acylating agent should be accomplished. Such separation can be effected before determination of total weight of the substituent groups present in the substituted succinic acylating agent. However, it is preferable to effect such separation after such determination using a mathematical correction of the result. The separation itself can be achieved using a silica gel column separation technique. A low molecular weight non-polar hydrocarbon solvent, such as hexane and more preferably pentane, is used as the solvent whereby the unreactive component or diluent is readily eluted from the column. The substituted succinic acylating agent entrained in the column can then be recovered by use of a more polar elution solvent, preferably methanol/methylene dichloride.

Succinimides

The alkenyl succinimides of this invention are formed by heating an alkenyl succinic anhydride, acid, acid-ester, acid halide, or lower alkyl ester prepared as above, with one or more compounds having at least one primary or secondary amino group capable of forming an imide or amide group in the course of the reaction with such alkenyl succinic anhydride, acid, acid-ester, acid halide, or lower alkyl ester. Residual unsaturation in the alkenyl group of the resultant compounds may be used as a reaction site, if desired. For example the alkenyl substituent may be hydrogenated to form an alkyl substituent. Similarly the olefinic bond(s) in the alkenyl substituent may be sulfurized, halogenated, hydrohalogenated or the like.

Alternatively, alkenyl succinimide derivatives of this invention can be formed by first reacting the alkenyl-substituted acylating agent formed as described above (e.g., in Examples 1-10) with a suitable reagent such as elemental sulfur and thereafter reacting the resultant sulfur-containing acylating agent with an amine reactant. Suitable procedures for effecting the reaction between sulfur and an alkenyl-substituted acylating agent are described in U.S. Pat. No. 3,309,316.

Because of the presence of at least one primary or secondary amino group in the compounds being acylated in the process, such compounds are herein referred to as "amine reactants". The amine reactants comprise various types of compounds such as amines, ureas, thioureas, aminoalcohols, aminophenols, and other primary and/or secondary amino-substituted compounds. The preferred amine reactants are polyamines containing at least one primary amino group.

The amine reactants can be widely diverse in chemical structure, and include straight, branched chain, and cyclic amines which can be unsubstituted or substituted with other functional groups, such as one or more ester groups, ether linkages, carbonyl groups, oxirane groups, carboxyl groups, thioether linkages, sulfhydryl groups, hydroxyl groups, and many others.

A few representative examples of amine reactants which may be employed in forming the ashless dispersants of this invention include straight or branched-chain alkanes containing two or more amino groups at least one of which is a primary amino group, such as 1,6-diaminooctane, 1,8-diaminooctane, 1,5,9-triaminononane, tetraaminoneopentane, etc.; polyaminoalkanols such as 2-(2-aminoethylamino)-ethanol and 2-[2-(2-aminoethylamino)-ethylamino]-ethanol; heterocyclic compounds containing two or more amino groups at least one of which is a primary amino group such as 1-(β-aminoethyl)-2-imidazolidone, 2-(2-aminoethylamino)-5-nitropyridine, 3-amino-N-ethylpiperidine, 2-(2-aminoethyl)-pyridine, 5-aminoindole, 3-amino-5-mercapto-1,2,4-triazole, and 4-(aminomethyl)-piperidine; the alkylene polyamines such as 1,2-propylene diamine, di-(1,2-propylene)triamine, di-(1,3-propylene)-triamine, N,N-dimethyl-1,3-propanediamine, 1,4-butanediamine, di-(1,2-butylene)triamine, N-(2-aminoethyl)-1,3-propanediamine, hexamethylenediamine and tetra-(1,2-propylene)pentamine; the hydroxyamines such as tris(hydroxymethyl)aminomethane, isopropanol amine, N-(2-hydroxyethyl)-1,3-propanediamine, N-2-hydroxypropyl ethylene diamine, N-aminoethylethanolamine, 4-aminophenol: the aromatic polyamines such as p-phenylene diamine, etc.; and the like.

Other useful amines include polyoxyalkylene polyamines such as those depicted by the formulas

$$NH_2\text{-alkylene-(O-alkylene)}_m\text{—}NH_2 \quad (II)$$

where the alkylene groups can be the same or different straight or branched chain groups containing 2 to 8 and preferably 2 to 4 carbon atoms each, and m is from 3 to 70 and preferably 10 to 35; and

$$R\text{-[alkylene-(O-alkylene)}_n\text{—}NH_2]_q \quad (III)$$

where the alkylene groups can be the same or different straight or branched chain groups containing 2 to 8 and preferably 2 to 4 carbon atoms each, R is a substituted hydrocarbon group, usually a saturated hydrocarbon group, of up to 10 carbon atoms, q represents the number of the depicted substituents on R and is from 3 to 6, and n is from 1 to 40 with the proviso that the sum of the n's is from 3 to about 70 and preferably from about 6 to about 35.

The polyoxyalkylene amines such as are depicted in Formula II or III, for example the polyoxyalkylene diamines and polyoxyalkylene triamines, may have various number average molecular weights, typically in the range of about 200 to about 4,000 and preferably in the range of about 200 to about 2,000. Polyoxyalkylene polyamines are available as articles of commerce, and may be obtained for example from the Jefferson Chemical Company, Inc. under the trade designations Jeffamine D,230, Jeffamine D-400, Jeffamine D-1000, Jeffamine D2000, Jeffamine T-403, etc.

Another group of polyoxyalkylene polyamines are those represented by the formula

$$R\text{—}C(O)\text{—}C(R)H\text{—}CH_2\text{—}C(O)\text{—}R \quad (IV)$$

wherein R is —NH—(alkylene—O)$_n$alkylene-NH$_2$ and n is 2 or 3. The alkylene groups can be the same or different, straight or branched chain groups containing 2 to 8 and preferably 2 to 4 carbon atoms each. These compounds are formed by reacting 3 to about 3.5 moles of a dicarboxylic acid reactant such as maleic acid, fumaric acid, or their anhydrides or C$_{1-4}$ dialkyl esters with a polyoxyalkylene diamine of the formula H$_2$N-(alkylene-O)$_n$-alkylene-NH$_2$ wherein alkylene and n are as just defined. Methods suitable for preparing such polyoxyalkylene polyamines are set forth for example in European Patent Publication No. EP 435,497.

Another type of amine reactants which can be used in forming the carboxylic derivatives of this invention are the amido-amine adducts such as are described in U.S. Pat. No. 5,034,018.

The most preferred amines are the ethylene polyamines which can be depicted by the formula

$$H_2N(CH_2CH_2NH)_nH \quad (V)$$

wherein n is an integer from one to about ten. These include: ethylene diamine, diethylene triamine, triethylene tetramine, tetraethylene pentamine, pentaethylene hexamine, and the like, including mixtures thereof in which case n is the average value of the mixture. These ethylene polyamines have a primary amine group at each end so can form mono-alkenylsuccinimides and bis-alkenylsuccinimides. Commercially available ethylene polyamine mixtures usually contain minor amounts of branched species and cyclic species such as N-aminoethyl piperazine, N,N'-bis(aminoethyl)piperazine, N,N'-bis(piperazinyl)ethane, and like compounds. The preferred commercial mixtures have approximate overall compositions falling in the range corresponding to diethylene triamine to pentaethylene hexamine, mixtures generally corresponding in overall makeup to tetraethylene pentamine being most preferred. Various suitable low cost polyethylene polyamine mixtures are available under various trade designations such as "Polyamine H", "Polyamine 400", "Dow Polyamine E-100", "Dow S-1107", etc. Methods for the production of polyalkylene polyamines are known and reported in the literature. See for example U.S. Pat. Nos. 4,827,037; 4,983,736; EP Nos. 412,611; 412,612; 412,613; 412,614; and 412,615, and references cited therein, all disclosures of such patent and cited references being incorporated herein by reference.

Particularly preferred ashless dispersants of the present invention are the products of reaction of polyethylene polyamine mixtures such as are available as articles of commerce, e.g., a mixture of linear, branched and cyclic species approximating (i) triethylene tetramine, (ii) tetraethylene pentamine, (iii) pentaethylene hexamine, or (iv) a mixture of any two or all three of (i), (ii), and (iii).

As used herein the term "succinimide" is meant to encompass the completed reaction product from reaction between the amine reactant(s) and the hydrocarbon-substituted carboxylic acid or anhydride (or like acid derivative) reactant(s), and is intended to encompass compounds wherein the product may have amide, amidine, and/or salt linkages in addition to the imide linkage of the type that results from the reaction of a primary amino group and an anhydride moiety.

Succinic Esters

Another group of carboxylic ashless dispersants of this invention includes the alkenyl succinic acid esters, diesters and esteramides of alcohols such as alcohols containing 1-100 carbon atoms and 1-10 hydroxyl groups and alkenyl succinic acid esters, diesters and ester-amides of phenols such as phenolic compounds containing 6-100 carbon atoms and 1-10 hydroxyl groups. The alkenyl succinic portion of these esters and ester-amides corresponds to the alkenyl succinic portion of the succinimides described above. As in the case of the succinimides, the alkenyl group can be hydrogenated or subjected to other reactions involving olefinic double bonds. Alternatively, the alkenyl group of the alkenyl-substituted acylating agent formed as described above (e.g., in Examples 1-10) can be reacted with a suitable reagent such as elemental sulfur and thereafter used to form the succinic ester or ester-amide. Reference may be had to U.S. Pat. No. 3,309,316 for a description of suitable procedures for effecting the reaction between sulfur and an alkenyl-substituted acylating agent.

The alcohol and phenol reactants can be used singly or in combinations, including combinations of monohydric alcohols, combinations of polyhydric alcohols, combinations of monohydric phenols, combinations of polyhydric phenols, combinations of at least one monohydric alcohol and at least one polyhydric alcohol, combinations of at least one monohydric phenol and at least one polyhydric phenol, combinations of at least one monohydric alcohol and at least one polyhydric phenol, combinations of at least one polyhydric alcohol and at least one monohydric phenol, combinations of at least one monohydric alcohol, at least one polyhydric alcohol and at least one monohydric phenol, combinations of at least one monohydric alcohol, at least one polyhydric alcohol and at least one polyhydric phenol, combinations of at least one monohydric phenol, at least one polyhydric phenol and at least one monohydric alcohol, combinations of at least one monohydric phenol, at least one polyhydric phenol and at least one polyhydric alcohol, and combinations of at least one monohydric alcohol, at least one polyhydric alcohol, at least one monohydric phenol and at least one polyhydric phenol. Polyhydric alcohols (often referred to as polyols) are the most preferred reactants for forming the esters and ester-amides of this invention.

The alcohols can be widely diverse in chemical structure, and include straight and branched chain alcohols which can be unsubstituted or substituted with other functional groups, such as one or more ester groups, ether linkages, carbonyl groups, oxirane groups, carboxyl groups, thioether linkages, sulfhydryl groups, and many others.

Typical alcohols which can be used in preparing the esters include ethylene glycol, diethylene glycol, tetraethylene glycol, diethylene glycol monoethylether, propylene glycol, tripropylene glycol, glycerol, sorbitol, monomethyl ether of glycerol, 1,1,1-trimethylol ethane, 1,1,1-trimethylol propane, 1,1,1-trimethylol butane, pentaerythritol, dipentaerythritol, tripentaerythritol, 9,10-dihydroxystearic acid, 3-chloro-1,2-propanediol, 1,2-butanediol, 2,3-hexanediol, pinacol, mannitol, 1,2-cyclohexanediol, 1,4-cyclohexanediol, cyclohexanedimethanol, glucose, mannose, triethanolamine, trioctanolamine, erythritol, higher molecular weight polyoxyalkylene glycols (e.g., polyoxyethylene glycols, polyoxypropylene glycols, mixed oxyethylene-oxypropylene glycols, etc.), glycerine-initiated polyoxyalkylene triols, and the like.

Typical phenols which can be used include such compounds as catechol, resorcinol, hydroquinone, tert-butylhydroquinone, 4-hydroxymethylphenol, 1,4-dihydroxnaphthalene, 4,4'-biphenol, 4,4'-methylenebisphenol, bisphenol-A, sym-trihydroxybenzene,4-(1,1,3,3-tetramethylbutyl)catechol, 3,3',4,4'-tetrahydroxydiphenyl, 4-(dimethylamino)phenol, 4-(diethylaminomethyl)phenol, 4-(2-hydroxyethoxyethoxy)phenol, and many other similar compounds.

Also useful in forming the succinic esters and ester amides of this invention are the heterocyclic polyols of the type described in European Patent Publication No. EP 288,324.

Preferred succinic esters of this invention are made using as a polyhydric alcohol having 3 to 20 carbon atoms such as one or a mixture of such compounds as glycerol, erythritol, pentaerythritol, dipentaerythritol, triipentaerythritol, gluconic acid, glyceraldehyde, glucose, arabinose, 1,7-heptanediol, 2,4-heptanediol, 1,2,3-hexanetriol, 1,2,4-hexanetriol, 1,2,5-hexanetriol, 2,3,4-hexanetriol, 1,2,3-butanetriol, 1,2,4-butane triol, quinic acid, 2,2,6,6-tetrakis(hydroxymethyl)cyclohexanol, 1,10-decanediol, digitalose, and the like. The succinic esters made from aliphatic alcohols having at least three hydroxyl groups and up to about 18 carbon atoms are particularly preferred.

The succinic esters are readily made by merely heating a mixture of a succinic acylating agent prepared as described above (e.g., alkenyl succinic acid, anhydride or lower alkyl ester such as a $C_1$-$C_4$ ester) with the alcohol while distilling out water or lower alkanol. In the case of acid-esters less alcohol is used. In fact, acid-esters made from alkenyl succinic anhydrides do not evolve water. In another method the alkenyl succinic acid or anhydrides can be merely reacted with an appropriate alkylene oxide such as ethylene oxide, propylene oxide, and the like, including mixtures thereof.

To form the alkenyl succinic ester-amides of this invention, the above-described alkenyl succinic acids, anhydrides or lower alkyl esters or etc. are heated with an alcohol and an amine either sequentially or in a mixture. The alcohols and amine reactants described above are also useful in this embodiment. Alternatively, amino alcohols and/or aminophenols can be used alone or with the alcohol and/or amine reactant to form ester-amide mixtures. The amino alcohol can contain up to 100 carbon atoms, 1-10 hydroxy groups and 1-6 amine nitrogen atoms. Examples are ethanolamine, 2-amino-2-methyl-1-propanol, 4-(2-hydroxyethyl)aniline, 2-aminopropanol, diethanolamine, 3-amino-1-propanol, 2-amino-2-methyl-1,3-propanediol, 2-amino-2-ethyl-1,3-propanediol, N-(2-hydroxypropyl)-N'-(2-aminoethyl)-piperazine, tris(hydroxymethyl)aminomethane (also known as tris(methylol)aminomethane), 2-amino-1-butanol, N-ethanol-diethylene triamine, and the like, including mixtures of two or more such substances.

Here again, the alkenyl group of the succinic ester-amide can be hydrogenated or subjected to other reactions involving olefinic double bonds.

A sub-category of carboxylic ashless dispersants of this invention comprises the Mannich-based derivatives of hydroxyaryl succinimides. Such compounds can be made by reacting a succinic acylating agent prepared as described above with an aminophenol to produce an N-(hydroxyaryl) hydrocarbyl succinimide which is then reacted with an alkylene diamine or polyalkylene polyamine and an aldehyde (e.g., formaldehyde), in a Mannich-base reaction. In conducting such a process, reaction conditions such as are set forth in U.S. Pat. No. 4,354,950, can be used. Accordingly, in the interest of brevity, the disclosure of U.S. Pat. No. 4,354,950 is incorporated herein by reference. As in the case of the other carboxylic ashless dispersants discussed above, the succinic acylating agent is formed as described above using a polyolefin, preferably a polyisobutene, having a number average molecular weight of 500 to 5,000, preferably 700 to 2,500, more preferably 700 to 1,400, and especially 800 to 1,200. Likewise, residual unsaturation in the polyalkenyl substituent group can be used as a reaction site as for example, by hydrogenation, sulfurization, or the like.

Reaction Conditions

The reaction between the succinic acylating agent and the amine reactant(s) and/or the alcohol reactant(s) is carried out under conventional reaction conditions. Thus in preparing a succinimide of this invention at least 0.5 equivalent (i.e., 1 mole) of the acylating agent reacts per equivalent of reactive primary and/or secondary amino groups present in the amine reactant(s). For example, from 1 to 2 moles of the acylating agent can react with one mole of a diamine having two reactive primary amino groups (and thus two equivalents of reactive amino groups). Similarly, from 1 to 4 moles of the acylating agent can react with one mole of an amine having four reactive primary amino groups (and thus four equivalents of reactive amino groups). In preparing a succinic ester of this invention at least one mole of the acylating agent reacts per equivalent of reactive hydroxyl groups present in the alcohol reactant(s). For example, from 1 to 4 moles of the acylating agent can react with one mole of a diol having two reactive hydroxyl groups per molecule. Ester-amides of this invention are formed by suitably proportioning the amine reactant(s) and alcohol reactant(s) so as to form an acylated product in which at least some of the hydroxyl groups and at least some of the primary amino groups are acylated.

Thus the reactants are proportioned to achieve the desired extent of acylation in the product according to well known principles. With a polyalkylene polyamine having approximately two reactive primary amino groups per molecule the amount of succinic acylating agent used is generally such as to cause at least 1.6 succinic groups to react per molecule of the polyamine. Likewise, with a polyol having at least two reactive hydroxyl groups per molecule, the amount of succinic acylating agent used is generally such as to cause at least 1.6 succinic groups to react per molecule of the polyol.

Reaction temperatures used in forming the succinic derivatives of this invention (i.e., the succinimides, succinic esters, and succinic ester-amides) are those sufficient to cause the desired reactions to occur. Generally speaking, the reactions are usually carried out at temperatures falling within the range of about 100° to about 250° C., and preferably in the range of about 140° to about 180° C. Water formed in the reaction is generally stripped from the reaction mixture during or after the reaction.

The succinic derivative compositions of this invention are either oil-soluble, or dissolvable in oil with the aid of a suitable solvent, or are oil-dispersible in the sense that they form stable dispersions in oil. Oil-soluble, dissolvable or oil-dispersible as that terminology is used herein does not necessarily indicate that the materials are soluble, dissolvable, miscible, or capable of being suspended in oil in all proportions. It does mean however that the additives are, for example, soluble or oil-dispersible to an extent sufficient to exert their intended effect in the environment in which the oil is employed. Moreover, the additional incorporation of other additives may also permit the incorporation of higher levels of a particular succinic derivative composition hereof, if desired.

The practice and advantages of this invention will become still further apparent from the following illustrative examples, which are not intended to limit, and should not be construed as limiting, the scope of this invention.

EXAMPLE A-1

Polyisobutenylsuccinic anhydride formed as in Example 1 and tetraethylene pentamine (Dow S1107) in a mole ratio of 1.8:1 are reacted at 165°–170° C. for 4 hours.

EXAMPLE A-2

The procedure of Example A-1 is repeated substituting triethylene tetramine (Union Carbide) for the tetraethylene pentamine.

EXAMPLE A-3

Polyisobutenylsuccinic anhydride formed as in Example 2 and tetraethylene pentamine (Dow S1107) in a mole ratio of 1.8:1 are reacted at 165°–170° C. for 2 hours.

EXAMPLE A-4

The procedure of Example A-3 is repeated substituting pentaethylene hexamine for the tetraethylene pentamine.

EXAMPLE A-5

Polyisobutenylsuccinic anhydride formed as in Example 3 and tetraethylene pentamine (Dow S1107) in a mole ratio of 1.8:1 are reacted at 165°–170° C. for 3 hours.

EXAMPLE A-6

The procedure of Example A-5 is repeated substituting pentaethylene hexamine for the tetraethylene pentamine.

EXAMPLE A-7

Polyisobutenylsuccinic anhydride formed as in Example 4 and tetraethylene pentamine (Dow S1107) in a mole ratio of 2:1 are reacted at 165° C. for 2.5 hours.

EXAMPLE A-8

The procedure of Example A-7 is repeated substituting triethylene tetramine for the tetraethylene pentamine.

EXAMPLE A-9

Polyisobutenylsuccinic anhydride formed as in Example 5 and tetraethylene pentamine (Dow S1107) in a mole ratio of 1.6:1 are reacted at 165° C. for 3 hours.

EXAMPLE A-10

The procedure of Example A-9 is repeated substituting triethylene tetramine for the tetraethylene pentamine.

EXAMPLE A-11

Polyisobutenylsuccinic anhydride formed as in Example 10 and tetraethylene pentamine (Dow S1107) in a mole ratio of 1.8:1 are reacted at 165° C. for 2 hours.

EXAMPLE A-12

The procedure of Example A-11 is repeated substituting triethylene tetramine (Dow) for the tetraethylene pentamine.

EXAMPLE A-13

The procedure of Example A-11 is repeated substituting pentaethylene hexamine for the tetraethylene pentamine.

EXAMPLE A-14

Polyisobutenylsuccinic anhydride (170 parts) formed as in Example 10 and pentaerythritol (68 parts) are reacted at 200° to 225° C. for 4 hours in 200 parts of process oil. The reaction mixture is cooled to 160° C. and 10 parts of tetraethylene pentamine (Dow S1107) is added and the reaction mixture maintained at 165° C. for 1 hour.

EXAMPLE A-15

The procedure of Example A-14 is repeated substituting 60 parts of tris(hydroxymethyl)aminomethane for the tetraethylene pentamine.

EXAMPLE A-16

In a first stage reaction, polyisobutenylsuccinic anhydride (PIBSA) formed as in Example 10 and tetraethylene pentamine (TEPA) in a mole ratio of 1.8:1 are reacted at 165°-170° C. for 4 hours. In a second stage reaction, maleic anhydride (MA) is added to the first stage reaction product in amount equivalent to 0.3 moles per mole of TEPA used in the first stage and the resultant mixture is heated at 165°-170° C. for 1.5 hours. The succinimide is thus formed using a total mole ratio of anhydrides to TEPA of 2.1:1. To provide a handleable concentrate, the reaction product is suitably diluted with 100 solvent neutral mineral oil such that the nitrogen content of the blend is about 1.8%.

EXAMPLE A-17

In a first stage reaction, PIBSA formed as in Example 10 and TEPA in a mole ratio of 2.05:1 are reacted at 165°-170° C. for 4 hours. In a second stage reaction, maleic acid is added to the first stage reaction product in amount equivalent to one mole per mole of TEPA used in the first stage and the resultant mixture is heated at 165°-170° C. for 1.5 hours. As in Example A-16, the reaction product is suitably diluted with mineral oil base stock to provide a handleable concentrate.

EXAMPLE A-18

The procedure of Example A-17 is repeated except that fumaric acid is used in the second stage in amount equivalent to a mole ratio of 1:1 relative to the TEPA used in the first stage.

EXAMPLE A-19

The procedure of Example A-18 is repeated using an equivalent amount of malic acid in lieu of fumaric acid in the second stage.

EXAMPLE A-20

The procedure of Example A-19 is repeated using in the second stage an equivalent amount of succinic acid in lieu of malic acid.

EXAMPLE A-21

A mixture is formed from 260 parts of a succinimide ashless dispersant formed as in Example A-1, 100 parts of a 100 Solvent Neutral refined mineral oil diluent, 8 parts of phosphorous acid ($H_3PO_3$) in the form of solid flakes, 3.5 parts of tolutriazole, 8 parts of boric acid, and 3.0 parts of water. The mixture is heated at 100° C. for two hours until all of the solid materials are dissolved. A vacuum of 40 mm Hg is gradually drawn on the product to remove the water while the temperature is slowly raised to 110° C. A clear solution or composition is obtained which is soluble in oil.

EXAMPLE A-22

The procedure of Example A-21 is repeated except that dibutyl hydrogen phosphite (26 parts) and water (10 parts) are used in lieu of the phosphorous acid, and the amount of boric acid used is 10 parts.

EXAMPLE A-23

The procedure of Example A-21 is repeated except that the boric acid and water are omitted.

EXAMPLE A-24

The procedure of Example A-21 is repeated except that the phosphorous acid is omitted.

EXAMPLE A-25

In a first stage reaction, polyisobutenylsuccinic anhydride (PIBSA) formed as in Example 10 and TEPA in a mole ratio of 1.8:1 are reacted at 165°-170° C. for 4 hours. In a second stage reaction, maleic anhydride (MA) is added to the first stage reaction product in amount equivalent to 0.3 mole per mole of TEPA used in the first stage and the resultant mixture is heated at 165° to 170° C. for 1.5 hours after which oil is added. In a third stage reaction, boric acid is added to the second stage reaction mixture at a temperature of 150°-155° C. in an amount corresponding to 4.0 moles per mole of TEPA initially employed. The mixture is heated at 150° C. for one hour and then water formed in the third stage reaction is removed by applying a vacuum of 40 mm for one hour. The resulting succinimide is both acylated and boronated.

EXAMPLE A-26

The procedure of Example A-25 is repeated using a chemically equivalent amount of the succinic ester-amide of Example A-14 in place of the succinimide. The resultant succinic ester-amide is both acylated and boronated.

EXAMPLE A-27

Stage A: A mixture of 2,100 parts of PIBSA produced as in Example 7, 290 parts of pentaerythritol, and 4,000 parts of process oil is heated at 225° to 235° C. for 5 hours.

Stage B: To 1,200 parts of the product mixture of Stage A maintained at 80° C. is added 60 parts of process oil and 10 parts of pyridine. The mixture is then heated at 100° to 120° C. for 2.5 hours and then stripped to 170° C. under vacuum. The residue is an oil solution of a post-treated product of this invention.

Stage C: To another 1,200 parts of the product mixture of Stage A is added 36 parts of maleic anhydride and the resulting mixture is heated to 200° C. over a 1.5 hour period. During the last ½ hour the mixture is blown with nitrogen. The product is then stripped under vacuum to yield an oil solution of a post-treated product of this invention.

As is clearly evident from many of the above examples, the ashless dispersants of this invention, i.e., the succinimides, succinic esters, and succinic ester-amides, formed from the acylating agents described hereinabove (for instance in Examples 1–10 hereinabove) can be subjected to a wide variety of subsequent reactions with post-treating agents. Typical post-treating agents, the conditions under which post-treatments are effected therewith, and typical improvements realized by such post-treatments are summarized below in Table 4 with reference to prior disclosures dealing with post-treatment of succinimides, succinic esters, and/or succinic ester-amides formed from conventional acylating agents. Thus in the practice of this invention, the post-treating agents of the prior disclosures are used in the manner described therein with the exception that in lieu of a conventional succinimide, succinic ester, and/or succinic ester-amide, a succinimide, succinic ester, and/or succinic ester-amide of this invention is used as the starting material for the post-treatment. In addition, it is contemplated that the improvements realized by application of such post-treatments to the carboxylic derivative compositions of this invention will result, at least in some cases, in improvements not achieved in post-treating prior art succinimides, succinic esters and/or succinic ester-amides and/or in improvements of greater magnitude than achievable with the prior art disperants. In Table 4, all references to patent numbers are to U.S. patents except as otherwise specified.

TABLE 4

| Post-Treating Agents | Post-Treatments Pat. Nos. |
|---|---|
| Inorganic phosphorus acid or anhydride | 3,403,102; 3,502,677; 3,513,093; 4,615,826; 4,648,980 |
| Organic phosphorus compound | 3,403,102; 3,502,677; 3,511,780; 3,513,093; GB 1,153,161 GB 2,140,811 |
| Phosphorus pentasulfide | 3,184,411; 3,342,735 |
| Boron compound | 3,087,936; 3,254,025; 3,281,428; 3,282,955; 2,284,409; 2,284,410; 3,338,832; 3,344,069; 3,533,945; 3,658,836; 3,703,536; 3,718,663; 4,455,243; 4,652,387; |

TABLE 4-continued

| Post-Treating Agents | Post-Treatments Pat. Nos. |
|---|---|
| Mono- or polycarboxylic acid, anhydride, and/or acid halide | 3,185,704; 3,216,936; 3,245,908; 3,245,909; 3,245,910; 3,415,750; 3,639,242; 3,692,681; 3,708,522; 4,548,724; 4,927,562; 4,948,386; GB 1,065,595; GB 1,162,436; GB 2,140,811; EP 0,438,849 |
| Mono- or polyepoxide or thioepoxide | 3,367,943; 3,373,111; 3,579,450; 3,859,318; 5,026,495; 5,030,369 |
| Aldehyde or ketone | 3,369,021; 3,455,831; 3,455,832; 3,458,530; |
| Carbon disulfide | 3,200,107; 3,256,185 |
| Glycidol | 4,617,137; 4,631,070 |
| Urea, thiourea or guanidine | 3,312,619; 3,865,813; GB 1,065,595 |
| Organic sulfonic acid | 3,189,544; GB 2,140,811 |
| Alkenyl cyanide | 3,278,550; 3,366,569 |
| Diketene | 3,546,243 |
| A diisocyanate | 3,573,205 |
| Alkane sultone | 3,749,695 |
| 1,3-Dicarbonyl compound | 4,579,675 |
| Sulfate of alkoxylated alcohol or phenol | 3,954,639 |
| Cyclic lactone | 4,617,138; 4,645,515; 4,668,246; 4,963,275; 4,971,711 |
| Cyclic carbonate or thiocarbonate, linear monocarbonate or polycarbonate, or chloroformate | 4,612,132; 4,647,390; 4,648,886; 4,670,170 |
| Nitrogen-containing carboxylic acid | 4,971,598; GB 2,140,811 |
| Hydroxy-protected chlorodicarbonyloxy compound | 4,614,522 |
| Lactam, thiolactam, thiolactone or dithiolactone | 4,614,603; 4,666,460 |
| Cyclic carbamate, cyclic thiocarbamate or cyclic dithiocarbamate | 4,663,062; 4,666,459 |
| Hydroxyaliphatic carboxylic acid | 4,482,464; 4,521,318; 4,713,189 |
| Oxidizing agent | 4,379,064 |
| Combination of phosphorus pentasulfide and a polyalkylene polyamine | 3,185,647 |
| Combination of carboxylic acid or an aldehyde or ketone and sulfur or sulfur chloride | 3,390,086; 3,470,098 |
| Combination of a hydrazine and carbon disulfide | 3,519,564 |
| Combination of an aldehyde and a phenol | 3,649,229; 5,030,249; 5,039,307 |
| Combination of an aldehyde and an O,O-diester of dithiophosphoric acid | 3,865,740 |
| Combination of a hydroxyaliphatic carboxylic acid and a boric acid | 4,554,086 |
| Combination of a hydroxyaliphatic carboxylic acid, then formaldehyde | 4,636,322 |

TABLE 4-continued

Post-Treatments

| Post-Treating Agents | Pat. Nos. |
|---|---|
| and a phenol | |
| Combination of a hydroxyaliphatic carboxylic acid and then an aliphatic dicarboxylic acid | 4,633,064 |
| Combination of formaldehyde and a phenol, and then glycolic acid | 4,699,724 |
| Combination of a hydroxyaliphatic carboxylic acid or oxalic acid and then a diisocyanate | 4,713,191 |
| Combination of inorganic acid or anhydride of phosphorus or a partial or total sulfur analog thereof and a boron compound | 4,857,214 |
| Combination of an organic diacid, then an unsaturated fatty acid, and then a nitroso-aromatic amine, optionally followed by a boron compound and then a glycolating agent | 4,973,412 |
| Combination of an aldehyde and a triazole | 4,963,278 |
| Combination of an aldehyde and a triazole, then a boron compound | 4,981,492 |
| Combination of cyclic lactone and a boron compound | 4,963,275; 4,971,711 |

While this invention has been discussed with reference to use of polybutenes as the polyolefin reactant for producing the ashless dispersants of this invention, use can be made of other polyolefins having an end group configuration comparable to that depicted hereinabove, such as isopentene polymers, isohexene polymers, isobutene-propylene copolymers, isobutene-ethylene copolymers, isobutene-ethylene-propylene terpolymers, isobutene-amylene copolymers, and the like.

Also provided by this invention are compositions which comprise either at least one oil of lubricating viscosity or at least one liquid hydrocarbonaceous fuel and at least one succinic derivative composition (succinimide, succinic ester, succinic esteramide) of this invention. Such compositions include both additive concentrates or additive solutions and finished oleaginous compositions such as lubricants and functional fluids. Thus the proportions of the succinic derivative composition and the oil or fuel can very widely depending upon the nature of the composition being formed. Thus in one of its embodiments this invention provides a carboxylic derivative composition in admixture with at least one oil of lubricating viscostiy or at least one hydrocarbonaceous liquid fuel in weight proportions falling in the range of about 0.1:99.9 to about 99.9:0.1, and preferably in the range of about 0.5:99.5 to about 90:10, said carboxylic derivative composition being produced by reacting at least one substituted succinic acylating agent with a reactant selected from the group consisting of (1) at least one amine having at least one primary or secondary amino group, (2) at least one alcohol, and (3) a combination of at least one amine having at least one primary or secondary amino group and at least one alcohol, the components of (3) being reacted with said at least one substituted succinic acylating agent concurrently or sequentially in any order, said at least one succinic acylating agent being prepared by reacting (i) at least one substantially aliphatic polymer of at least one lower olefin, and (ii) an acidic reactant or a mixture of two or more acidic reactants represented by the general formula

R—CO—CH=CH—CO—R' wherein R and R' are independently —OH, —O-lower alkyl, a halogen atom, or taken together are a single oxygen atom; the process of preparing said at least one succinic acylating agent being characterized in that:

a) the substantially aliphatic polymer is comprised predominantly or entirely of polyisobutene, at least 50% of the polyisobutene content of such polymer having an end group represented by the formula

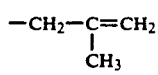

b) the mole ratio of said acidic reactant(s): said polymer(s) is at least 1:1; and
c) the reaction mixture is maintained under superatmospheric pressure during at least a substantial portion of the reaction period.

Preferred succinic derivative compositions for this use are formed from acylating agents of the type described above further characterized by having an average total tar rating as determined by the method described in the specification hereof that is at least about 40% lower, and most preferably at least 50% lower, than the average total tar rating of a corresponding product made in the same way under essentially the same reaction conditions using a polyisobutene containing less than 10% of the above-depicted end group. Particularly preferred succinic derivative compositions are those formed using acylating agents having a succination ratio of less than 1.3—i.e., the acylating agents have within their structure an average of less than 1.3 succinic groups per each substituent group derived from the aforesaid substantially aliphatic polymer.

The foregoing finished oleaginous compositions of this invention possess enhanced dispersant properties and thus are capable of being stored and used for long periods of time without excessive formation and deposition of sludge and/or other similar deposits. Accordingly, the finished lubricant and functional fluid compositions can be used in a wide variety of applications such as engine oils, manual and automatic transmission fluids, gear oils, tractor oils, cutting and machining oils, quenching oils, transformer oils, hydraulic fluids, general purpose lubricants, and the like. Similarly, the finished fuel compositions of this invention can be gasolines, diesel fuels, kerosene, home and/or industrial heating oils, burner fuels, gas oils, jet fuels, aviation fuels, gas turbine fuels, bunker fuels, etc., depending upon the volatility and viscosity characteristics of the hydrocarbonaceous fuel itself. Compositions in which the hydrocarbonaceous fuel is a distillate fuel in the boiling range of about 150° to about 800° F. are preferred.

In most cases, the finished lubricants and functional fluids of this invention will contain up to about 20% by weight of the succinic derivative composition, and in most cases the additive concentrates adapted for use in oils will contain up to about 80% by weight of one or more diluent oils of lubricating viscosity. Similarly the finished hydrocarbonaceous fuels of this invention will contain up to about 10% by weight of the succinic derivative composition, and in most cases the additive concentrates adapted for use in oils will contain up to about 90% by weight of one or more inert diluents or carriers, such as a light petroleum fraction, a light oil, a poly-α-olefin oligomer, a polyoxyalkylene glycol, a polyoxyalkylene monool, or the like.

Further embodiments of the present invention are additive concentrates and lubricant or functional fluid compositions containing particular combinations of one or more additive components (hereinafter described) together with a carboxylic derivative composition of this invention (i.e., a succinimide, succinic ester, and/or a succinic ester-amide, such as are illustrated in Examples A-1 through A-26 hereinabove. For convenience, these embodiments are referred to hereinbelow as Embodiments A, B, C, and D.

Embodiment A

One such embodiment is an oil of lubricating viscosity or an additive concentrate for use in oil of lubricating viscosity containing at least the following components:

1) one or more oil-soluble zinc hydrocarbyl dithiophosphates; and
2) a carboxylic derivative composition produced by reacting at least one substituted succinic acylating agent with a reactant selected from the group consisting of (1) at least one amine having at least one primary amino group, (2) at least one alcohol, and (3) a combination of at least one amine having at least one primary amino group and at least one alcohol, the components of (3) being reacted with said at least one substituted succinic acylating agent concurrently or sequentially in any order, said at least one succinic acylating agent being prepared by reacting (i) at least one substantially aliphatic polymer of at least one lower olefin, and (ii) an acidic reactant or a mixture of two or more acidic reactants represented by the general formula $$R-CO-CH=CH-CO-R'$$

wherein R and R' are independently —OH, —O-lower alkyl, a halogen atom, or taken together are a single oxygen atom; the process of preparing said at least one succinic acylating agent being characterized in that:

a) the substantially aliphatic polymer is comprised predominantly or entirely of polyisobutene, at least 50% of the polyisobutene content of such polymer having an end group represented by the formula

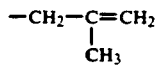

b) the mole ratio of said acidic reactant(s): said polymer(s) is at least 1:1; and
c) the reaction mixture is maintained under superatmospheric pressure during at least a substantial portion of the reaction period.

Preferred carboxylic derivative compositions are formed using acylating agents as described above that are further characterized by having (i) an average total tar rating as determined by the method described in the specification hereof that is at least about lower, and most preferably at least 50% lower, than the average total tar rating of a corresponding product made in the same way under essentially the same reaction conditions using a polyisobutene containing less than 10% of the above-depicted end group; and/or (ii) a succination ratio below 1.3.

The relative proportions of these components is preferably such that the weight ratio of phosphorus in 1) to nitrogen in 2) is in the range of from about 0.001:1 to about 100:1, and preferably in the range of about 0.01:1 to about 70:1. These combinations serve to inhibit wear; to inhibit deposit, varnish and/or sludge formation and/or deposition; and to protect the lubricant or functional fluid composition from premature oxidative degradation, especially at elevated temperatures. The quantity of these components 1) and 2) added to the base oil of lubricating viscosity (proportioned as described in this paragraph) is a minor dispersing amount, and is usually such that the amount of component 2) is in the range of about 0.01 to about 20% by weight of the total lubricating oil composition.

As is well known, zinc hydrocarbyl dithiophosphates are usually prepared by reacting phosphorus pentasulfide with one or more alcohols or phenolic compounds or diols to produce a hydrocarbyl dithiophosphoric acid which is then neutralized with one or more zinc-containing bases. When a monohydric alcohol or phenol is used in this reaction, the final product is a zinc dihydrocarbyl dithiophosphate. On the other hand, when a suitable diol (e.g., 2,4-pentanediol) is used in this reaction, the final product is a zinc salt of a cyclic hydrocarbyl dithiophosphoric acid. See, for example, U.S. Pat. No. 3,089,850. Thus typical oil-soluble zinc hydrocarbyl dithiophosphates used as component 1) may be represented by the formula

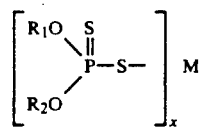

where $R_1$ and $R_2$ are, independently, hydrocarbyl groups or taken together are a single hydrocarbyl group forming a cyclic structure with the phosphorus and two oxygen atoms, preferably a hydrocarbyl-substituted trimethylene group of sufficient carbon content to render the compound oil soluble, M is zinc, and x is an integer corresponding to the valence of M. The preferred compounds are those in which $R_1$ and $R_2$ are separate hydrocarbyl groups (i.e., the zinc dihydrocarbyl dithiophosphates). Usually the hydrocarbyl groups of the zinc dihydrocarbyl dithiophosphates will contain no more than about 50 carbon atoms each although even higher molecular weight hydrocarbyl groups can be present in the compound. The hydrocarbyl groups include cyclic and acyclic groups, both saturated and unsaturated, such as alkyl, cycloalkyl, alkenyl, cycloalkenyl, aryl, cycloalkylalkyl, aralkyl, and the like. It will be understood that the hydrocarbyl groups may contain elements other than carbon and hydrogen provided such other elements do not detract from the predominantly hydrocarbonaceous character of the hydrocarbyl group. Thus the hydrocarbyl groups may contain ether oxygen atoms, thioether sulfur atoms, secondary or tertiary amino nitrogen atoms, and/or inert functional groups such as esterified carboxylic groups, keto groups, thioketo groups, and the like.

The phosphorodithioic acids from which the metal salts are formed can be prepared by the reaction of about 4 moles of one or more alcohols (cyclic or acyclic) or one or more phenols or mixture of one or more alcohols and one or more phenols (or about 2 moles of one or more diols) per mole of phosphorus pentasulfide, and the reaction may be carried out within a temperature range of from about 50° to about 200° C. The reaction generally is completed in about 1 to 10 hours. Hydrogen sulfide is liberated during the reaction.

The alcohols used in forming the phosphorodithioic acids by the above method are preferably primary alcohols, or secondary alcohols. Mixtures thereof are also suitable. The primary alcohols include propanol, butanol, isobutyl alcohol, pentanol, 2-ethyl-1-hexanol, isooctyl alcohol, nonanol, decanol, undecanol, dodecanol, tridecanol, tetradecanol, octadecanol, eicosanol, and the like. The primary alcohols may contain various substituent groups such as halogen atoms, nitro groups, etc., which do not interfere with the desired reaction. Among suitable secondary alcohols are included 2-butanol, 2-pentanol, 3-pentanol, 2-hexanol, 5-methyl-2-hexanol, and the like. In some cases, it is preferable to utilize mixtures of various alcohols, such as mixtures of 2-propanol with one or more higher molecular weight primary alcohols, especially primary alcohols having from 4 to about 13 carbon atoms in the molecule. Such mixtures preferably contain at least 10 mole percent of 2-propanol, and usually will contain from about 20 to about 90 mole percent of 2-propanol. In one preferred embodiment, the alcohol comprises about 30 to 50 mole percent of 2-propanol, about 30 to 50 mole percent isobutyl alcohol and about 10 to 30 mole percent of 2-ethyl-1-hexanol.

Other suitable mixtures of alcohols include 2-propanol/butanol;2-propanol/2-butanol;2-propanol/2-ethyl-1-hexanol;butanol/2-ethyl-1-hexanol; isobutyl alcohol/2-ethyl-1-hexanol; and 2-propanol/tridecanol.

Cycloaliphatic alcohols suitable for use in the production of the phosphorodithioic acids include cyclopentanol, cyclohexanol, methylcyclohexanol, cyclooctanol, borneol and the like. Preferably, such alcohols are used in combination with one or more primary alkanols such as butanol, isobutyl alcohol, or the like.

Illustrative phenols which can be employed in forming the phosphorodithioic acids include phenol, o-cresol, m-cresol, p-cresol, 4-ethylphenol, 2,4-xylenol, and the like. It is desirable to employ phenolic compounds in combination with primary alkanols such as propanol, butanol, hexanol, or the like.

Other alcohols which can be employed include benzyl alcohol, cyclohexenol, and their ring-alkylated analogs.

It will be appreciated that when mixtures of two or more alcohols and/or phenols are employed in forming the phosphorodithioic acid, the resultant product will normally comprise a mixture of three or more different dihydrocarbyl phosphorodithioic acids, usually in the form of a statistical distribution in relation to the number and proportions of alcohols and/or phenols used.

Illustrative diols which can be used in forming the phosphorodithioic acids include 2,4-pentanediol, 2,4-hexanediol, 3,5-heptanediol, 7-methyl-2,4-octanediol, neopentyl glycol, 2-butyl-1,3-propanediol, 2,2-diethyl-1,3-propanediol, and the like.

The preparation of the zinc salts of the dihydrocarbyl dithiophosphoric acids or the cyclic hydrocarbyl dithiophosphoric acids is usually effected by reacting the acid product with a suitable zinc compound such as zinc oxide, zinc carbonate, zinc hydroxide, zinc alkoxide, or other appropriate zinc salt. Simply mixing and heating such reactants is normally sufficient to cause the reaction to occur and the resulting product is usually of sufficient purity for use in the practice of this embodiment of the present invention. Typically, the salts are formed in the presence of a diluent such as an alcohol, water or a light mineral oil. Neutral salts are prepared by reacting one equivalent of the zinc oxide or hydroxide with one equivalent of the acid. Basic zinc salts are prepared by adding an excess (i.e., more than one equivalent) of the zinc oxide or hydroxide with one equivalent of the dihydrocarbyl phosphorodithioic acid or cyclic hydrocarbyl phosphorodithioic acid.

In some cases, incorporation of certain ingredients such as small amounts of zinc acetate or acetic acid in conjunction with the zinc reactant will facilitate the reaction and provide an improved product. For example, use of up to about 5% of zinc acetate in combination with the required amount of zinc oxide tends to facilitate the formation of zinc dihydrocarbyl dithiophosphates.

Examples of useful zinc salts of dihydrocarbyl dithiophosphoric acids, and methods for preparing such salts are found in the prior art such as for example, U.S. Pat. Nos. 4,263,150; 4,289,635; 4,308,154; 4,322,479; 4,417,990; and 4,466,895.

Generally speaking, the preferred types of zinc salts of dihydrocarbyl dithiophosphoric acids are the oil-soluble zinc salts of dialkyl dithiophosphoric acids. Such compounds generally contain alkyl groups having at least three carbon atoms, and preferably the alkyl groups contain up to 10 carbon atoms although as noted above, even higher molecular weight alkyl groups are entirely feasible. A few illustrative zinc dialkyl dithiophosphates include zinc diisopropyl dithiophosphate, zinc dibutyl dithiophosphate, zinc diisobutyl dithiophosphate, zinc di-sec-butyl dithiophosphate, the zinc dipentyl dithiophosphates, the zinc dihexyl dithiophosphates, the zinc diheptyl dithiophosphates, the zinc dioctyl dithiophosphates, the zinc dinonyl dithiophosphates, the zinc didecyl dithiophosphates, and the higher homologs thereof. Mixtures of two or more such zinc compounds are often preferred for use, such as zinc salts of dithiophosphoric acids formed from mixtures of isopropyl alcohol and secondary butyl alcohol; isopropyl alcohol, isobutyl alcohol, and 2-ethylhexyl alcohol; isopropyl alcohol, butyl alcohol, and pentyl alcohol; isobutyl alcohol and octyl alcohol; and the like.

Embodiment B

Another embodiment of this invention is an oil of lubricating viscosity or an additive concentrate for use in oil of lubricating viscosity containing at least the following components:

1) one or more oil-soluble or oil-dispersible alkali or alkaline-earth metal-containing detergents; and
2) a carboxylic derivative composition produced by reacting at least one substituted succinic acylating agent with a reactant selected from the group consisting of (1) at least one amine having at least one primary amino group, (2) at least one alcohol, and (3) a combination of at least one amine having at least one primary amino group and at least one alcohol, the components of (3) being reacted with said at least one substituted succinic acylating agent concurrently or sequentially in any order, said at least one succinic acylating agent being prepared by reacting (i) at least one substantially aliphatic polymer of at least one lower olefin, and (ii) an acidic reactant or a mixture of two or more acidic reactants represented by the general formula

R—CO—CH=CH—CO—R' wherein R and R' are independently —OH, —O-lower alkyl, a halogen atom, or taken together are a single oxygen atom; the process of preparing said at least one succinic acylating agent being characterized in that:
a) the substantially aliphatic polymer is comprised predominantly or entirely of polyisobutene, at least 50% of the polyisobutene content of such polymer having an end group represented by the formula

—CH$_2$—C=CH$_2$
  |
  CH$_3$ b) the mole ratio of said acidic reactant(s): said polymer(s) is at least 1:1; and
c) the reaction mixture is maintained under superatmospheric pressure during at least a substantial portion of the reaction period; and
3) optionally, one or more oil-soluble zinc hydrocarbyl dithiophosphates.

Preferred carboxylic derivative compositions are formed using acylating agents as described above that are further characterized by having (i) an average total tar rating as determined by the method described in the specification hereof that is at least about lower, and most preferably at least 50% lower, than the average total tar rating of a corresponding product made in the same way under essentially the same reaction conditions using a polyisobutene containing less than 10% of the above-depicted end group; and/or (ii) a succination ratio of less than 1.3.

It will be noted that in these compositions there are at least two required components, designated 1) and 2). This embodiment also includes a three-component mixture composed of the components designated as 1), 2) and 3). In these various combinations the relative proportions of these components is preferably such that the weight ratio of metal in 1) to nitrogen in 2) is in the range of from about 0.01:1 to about 1000:1, and preferably is in the range of from about 0.1:1 to about 700:1, and such that when component 3) is employed, the weight ratio of phosphorus in component 3) to nitrogen in component 2) is in the range of from about 0.001:1 to about 100:1, and preferably in the range of about 0.01:1 to about 70:1. These combinations serve to inhibit wear; to inhibit deposit, varnish and/or sludge formation and-/or deposition; and to protect the lubricant or functional fluid composition from premature oxidative degradation, especially at elevated temperatures. The quantity of these components 1) and 2), and optionally component 3) (proportioned as described in this paragraph) added to the base oil of lubricating viscosity is a minor dispersing amount, and is usually such that the amount of component 2) is in the range of about 0.01 to about 20% by weight of the total lubricating oil composition.

The metal-containing detergents which are employed in this embodiment are exemplified by oil-soluble or oil-dispersible basic salts of alkali or alkaline earth metals with one or more of the following acidic substances (or mixtures thereof): (1) sulfonic acids, (2) carboxylic acids, (3) salicylic acids, (4) alkylphenols, (5) sulfurized alkylphenols, (6) organic phosphorus acids characterized by at least one direct carbon-to-phosphorus linkage. Such organic phosphorus acids include those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium. The salts for use in this embodiment are preferably basic salts having a TBN of at least 50, preferably above 100, and most preferably above 200. In this connection, TBN is determined in accordance with ASTM D-2896-88.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature of about 50° C., and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, Cellosolve alcohol, Carbitol alcohol, ethylene glycol, stearyl alcohol, and cyclohexyl alcohol; and amines such as aniline, phenylenediamine, phenothiazine, phenyl-betanaphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60° to 200° C.

Examples of suitable metal-containing detergents include, but are not limited to, the basic or overbased salts of such substances as lithium phenates, sodium phenates, potassium phenates, calcium phenates, magnesium phenates, sulfurized lithium phenates, sulfurized sodium phenates, sulfurized potassium phenates, sulfurized calcium phenates, and sulfurized magnesium phenates wherein each aromatic group has one or more aliphatic groups to impart hydrocarbon solubility; lithium sulfonates, sodium sulfonates, potassium sulfonates, calcium sulfonates, and magnesium sulfonates wherein each sulfonic acid moiety is attached to an aromatic nucleus which in turn usually contains one or more aliphatic substituents to impart hydrocarbon solubility; lithium salicylates, sodium salicylates, potassium salicylates, calcium salicylates, and magnesium salicylates wherein the aromatic moiety is usually substituted by one or more aliphatic substituents to impart hydrocarbon solubility; the lithium, sodium, potassium, calcium and magnesium salts of hydrolyzed phosphosulfurized olefins having 10 to 2,000 carbon atoms or of hydrolyzed phosphosulfurized alcohols and/or aliphatic-substituted phenolic compounds having 10 to 2,000 carbon atoms; lithium, sodium, potassium, calcium and magnesium salts of aliphatic carboxylic acids and aliphatic-substituted cycloaliphatic carboxylic acids; and many other similar alkali and alkaline earth metal salts of oil-soluble organic acids. Mixtures of basic or overbased salts of two or more different alkali and/or alkaline earth metals can be used. Likewise, basic or overbased salts of mixtures of two or more different acids or two or more different types of acids (e.g., one or more calcium phenates with one or more calcium sulfonates) can also be used. While rubidium, cesium and strontium salts are feasible, their expense renders them impractical for most uses. Likewise, while barium salts are effective, the status of barium as a heavy metal under a toxicological cloud renders barium salts less preferred for present-day usage.

As is well known, overbased metal detergents are generally regarded as containing overbasing quantities of inorganic bases, probably in the form of micro dispersions or colloidal suspensions. Thus the terms "oil-soluble" and "oil-dispersible" are applied to these metal-containg detergents so as to include metal detergents wherein inorganic bases are present that are not necessarily completely or truly oil-soluble in the strict sense of the term, inasmuch as such detergents when mixed into base oils behave in much the same way as if they were fully and totally dissolved in the oil.

Collectively, the various basic or overbased detergents referred to hereinabove, have sometimes been called, quite simply, basic alkali metal or alkaline earth metal-containing organic acid salts.

Methods for the production of oil-soluble basic and overbased alkali and alkaline earth metal-containing detergents are well known to those skilled in the art and are extensively reported in the patent literature. See for example, the disclosures of U.S. Pat. Nos. 2,451,345; 2,451,346; 2,485,861; 2,501,731; 2,501,732; 2,585,520; 2,671,758; 2,616,904; 2,616,905; 2,616,906; 2,616,911; 2,616,924; 2,616,925; 2,617,049; 2,695,910; 3,178,368; 3,367,867; 3,496,105; 3,629,109; 3,865,737; 3,907,691; 4,100,085; 4,129,589; 4,137,184; 4,148,740; 4,212,752; 4,617,135; 4,647,387; 4,880,550; GB Published Patent Application 2,082,619 A, and European Patent Publication Nos. 121,024 B1 and 259,974 A2.

Embodiment C

Still another embodiment of this invention is an oil of lubricating viscosity or an additive concentrate for use in oil of lubricating viscosity containing at least the following components:

1) one or more oil-soluble or oil-dispersible sulfur-containing antiwear and/or extreme pressure agents; and
2) a carboxylic derivative composition produced by reacting at least one substituted succinic acylating agent with a reactant selected from the group consisting of (1) at least one amine having at least one primary amino group, (2) at least one alcohol, and (3) a combination of at least one amine having at least one primary amino group and at least one alcohol, the components of (3) being reacted with said at least one substituted succinic acylating agent concurrently or sequentially in any order, said at least one succinic acylating agent being prepared by reacting (i) at least one substantially aliphatic polymer of at least one lower olefin, and (ii) an acidic reactant or a mixture of two or more acidic reactants represented by the general formula

R—CO—CH=CH—CO—R' wherein R and R' are independently —OH, —O-lower alkyl, a halogen atom, or taken together are a single oxygen atom; the process of preparing said at least one succinic acylating agent being characterized in that:

a) the substantially aliphatic polymer is comprised predominantly or entirely of polyisobutene, at least 50% of the polyisobutene content of such polymer having an end group represented by the formula

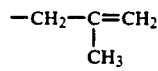

b) the mole ratio of said acidic reactant(s):said polymer(s) is at least 1:1; and
c) the reaction mixture is maintained under superatmospheric pressure during at least a substantial portion of the reaction period; and 3) optionally, one or more oil-soluble zinc hydrocarbyl dithiophosphates; and/or
4) optionally, one or more oil-soluble or oil-dispersible alkali or alkaline earth metal detergents.

Preferred carboxylic derivative compositions are formed using acylating agents as described above that are further characterized by having (i) an average total tar rating as determined by the method described in the specification hereof that is at least about lower, and most preferably at least 50% lower, than the average total tar rating of a corresponding product made in the same way under essentially the same reaction conditions using a polyisobutene containing less than 10% of the above-depicted end group; and/or (ii) a succination ratio below 1.3.

It will be noted that in these compositions there are at least two required components, designated 1) and 2). This embodiment also includes two three-component mixtures, the first composed of the components designated as 1), 2) and 3) and the second composed of the components designated as 1), 2) and 4). And additionally this embodiment comprises the four-component combinations composed of the components designated as 1), 2), 3) and 4). In these various combinations the relative proportions of these components is preferably such that the weight ratio of sulfur in 1) to nitrogen in 2) is in the range of from about 0.001:1 to about 100:1, and preferably in the range of about 0.01 to about 70:1; such that when component 3) is employed, the weight ratio of phosphorus as component 3) to nitrogen as component 2) is in the range of from about 0.001:1 to about 100:1, and preferably in the range of about 0.01:1 to about 70:1; and such that when component 4) is employed, the weight ratio of metal as component 4) to nitrogen as component 2) is in the range of from about 0.001:1 to about 1000:1, and preferably in the range of from about 0.1:1 to about 700:1. These combinations serve to inhibit wear; to inhibit deposit, varnish and/or sludge formation and/or deposition; and to protect the lubricant or functional fluid composition from premature oxidative degradation, especially at elevated temperatures. The quantity of these components 1) and 2), and optionally 3) and/or 4) (proportioned as described in this paragraph) added to the base oil of lubricating viscosity is a minor dispersing amount, and is usually such that the amount of component 2) is in the range of about 0.01 to about 20% by weight of the total lubricating oil composition.

Various types of sulfur-containing antiwear and/or extreme pressure agents can be used in the practice of Embodiment C. Examples are included within the categories of dihydrocarbyl polysulfides; sulfurized olefins; sulfurized fatty acid esters of both natural and synthetic origins; trithiones; sulfurized thienyl derivatives; sulfurized terpenes; sulfurized oligomers of $C_2$-$C_8$ monoolefins; and sulfurized Diels-Alder adducts such as those disclosed in U.S. Pat. No. Re. 27,331. Specific examples include sulfurized polyisobutene of Mn 1,100, sulfurized isobutylene, sulfurized diisobutylene, sulfurized triisobutylene, dicyclohexyl polysulfide, diphenyl polysulfide, dibenzyl polysulfide, dinonyl polysulfide, and mixtures of di-tert-butyl polysulfide such as mixtures of di-tert-butyl trisulfide, di-tert-butyl tetrasulfide and di-tert-butyl pentasulfide, among others. Combinations of such categories of sulfur-containing antiwear and/or extreme pressure agents can also be used, such as a combination of sulfurized isobutylene and di-tert-butyl trisulfide, a combination of sulfurized isobutylene and dinonyl trisulfide, a combination of sulfurized tall oil and dibenzyl polysulfide, and the like.

One type of sulfur-containing antiwear and/or extreme pressure agents is comprised of the oil-soluble active sulfur-containing antiwear and/or extreme pressure agents. Generally speaking, these are substances which possess a linkage of two or more sulfur atoms (e.g., —S—S—, —S—S—S—, —S—S—S—S—, S—S—S—S—S—, etc.).

To determine whether a sulfur-containing material is an active sulfur-containing material, use is made of a copper coupon corrosion test conducted as follows: A copper coupon approximately $70 \times 15$ mm and about 1.25 mm in thickness is cleaned by use of steel wool (0000 grade), washed with heptane, and then with acetone, dried, and weighed to the nearest 0.1 mg. The cleaned coupon is placed in a test tube and covered completely with the composition to be tested, and the system is heated to 125° C. by means of an oil bath. After holding the system at 125° C. for three hours, the copper coupon is removed from the test tube, rinsed with heptane, and then with acetone. The dried coupon is then rubbed with a paper towel moistened with acetone to remove any surface flakes formed by copper corrosion. The coupon is then air-dried and weighed to the nearest 0.1 mg. The difference in weight between the initial copper coupon and the coupon after the test represents the extent to which the copper was corroded under the test conditions. Therefore the larger the weight difference, the greater the copper corrosion, and thus the more active the sulfur compound. If the coupon weight loss is 30 milligrams or more, the sulfur-containing agent is considered "active".

Another type of sulfur-containing antiwear and/or extreme pressure agents suitable for use in the practice of this invention is comprised of "non-active" sulfur-containing additives. These are materials which when subjected to the above copper coupon corrosion test give a weight loss of less than 30 milligrams. Examples of materials falling in this category include Anglamol 33 additive (a sulfurized isobutylene product of The Lubrizol Corporation), distilled di-tert-butyl trisulfide, and the like.

Because of the toxicity of hydrogen sulfide, it is preferable, though not essential, to utilize in the practice of this invention oil-soluble sulfur-containing antiwear and/or extreme pressure agents, and more preferably oil-soluble active sulfur-containing antiwear and/or extreme pressure agents, that yield less than 25 ppm, and more preferably less than 10 ppm, of vapor space $H_2S$ when heated in the concentrated state for one week at 65° C. Most preferred are materials of this type which yield no detectable vapor space $H_2S$ when tested under these conditions.

The most preferred oil-soluble metal-free sulfur-containing antiwear and/or extreme pressure agents from the cost-effectiveness standpoint are the sulfurized olefins containing at least 30% by weight of sulfur, the dihydrocarbyl polysulfides containing at least 25% by weight of sulfur, and mixtures of such sulfurized olefins and polysulfides. Of these materials, sulfurized isobutylene having a sulfur content of at least 40% by weight and a chlorine content of less than 0.2% by weight is the most especially preferred material. Methods of preparing sulfurized olefins are described in U.S. Pat. Nos. 2,995,569; 3,673,090; 3,703,504; 3,703,505; 3,796,661; and 3,873,454. Also useful are the sulfurized olefin derivatives described in U.S. Pat. No. 4,654,156.

When including component 3) in the practice of Embodiment C, use can be made of any of the zinc hydrocarbyl dithiophosphates referred to hereinabove with reference to Embodiment A.

Embodiment D

A still further embodiment of this invention is an oil of lubricating viscosity or an additive concentrate for use in oil of lubricating viscosity containing at least the following components:

1) at least one oil-soluble metal-free phosphorus-containing (preferably phosphorus- and nitrogen-containing) antiwear and/or extreme pressure agent, most preferably an amine salt of at least one dihydrocarbyl ester of a thiophosphoric acid; and 2) a carboxylic derivative composition produced by reacting at least one substituted succinic acylating agent with a reactant selected from the group consisting of (1) at least one amine having at least one primary amino group, (2) at least one alcohol, and (3) a combination of at least one amine having at least one primary amino group and at least one alcohol, the components of (3) being reacted with said at least one substituted succinic acylating agent concurrently or sequentially in any order, said at least one succinic acylating agent being prepared by reacting (i) at least one substantially aliphatic polymer of at least one lower olefin, and (ii) an acidic reactant or a mixture of two or more acidic reactants represented by the general formula

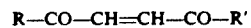

wherein R and R' are independently —OH, —O-lower alkyl, a halogen atom, or taken together are a single oxygen atom; the process of preparing said at least one succinic acylating agent being characterized in that:

a) the substantially aliphatic polymer is comprised predominantly or entirely of polyisobutene, at least 50% of the polyisobutene content of such polymer having an end group represented by the formula

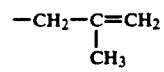

b) the mole ratio of said acidic reactant(s):said polymer(s) is at least 1:1; and c) the reaction mixture is maintained under superatmospheric pressure during at least a substantial portion of the reaction period; and 3) optionally, one or more oil-soluble or oil-dispersible sulfur-containing antiwear and/or extreme pressure agents.

Preferred carboxylic derivative compositions of this embodiment are produced using acylating agents as described above that are further characterized by having (i) an average total tar rating as determined by the method described in the specification hereof that is at least about 40% lower, and most preferably at least 50% lower, than the average total tar rating of a corresponding product made in the same way under essentially the same reaction conditions using a polyisobutene containing less than 10% of the above-depicted end group; and/or (ii) a succination ratio below 1.3.

It will be noted that in these compositions there are at least two required components, designated 1) and 2). This embodiment also includes three-component mixtures composed of the components designated as 1), 2) and 3). In these various combinations the relative proportions of these components is preferably such that the weight ratio of phosphorus in 1) to nitrogen in 2) is in the range of from about 0.001:1 to about 100:1, and preferably in the range of about 0.01:1 to about 70:1; and such that when component 3) is employed, the weight ratio of sulfur in component 3) to nitrogen in component 2) is in the range of from about is in the range of from about 0.001:1 to about 100:1, and preferably in the range of about 0.01 to about 70:1. These combinations serve to inhibit wear and to inhibit deposit, varnish and/or sludge formation and/or deposition. The quantity of these components 1) and 2), and optionally 3) (proportioned as described in this paragraph) added to the base oil of lubricating viscosity is a minor dispersing amount, and is usually such that the amount of component 2) is in the range of about 0.01 to about 20% by weight of the total lubricating oil composition.

For purposes of this invention a component which contains both phosphorus and sulfur in irs chemical structure is deemed a phosphorus-containing antiwear and/or extreme pressure agent rather than a sulfur-containing antiwear and/or extreme pressure agent.

Although use can be made of a wide variety of oil-soluble substances such as the oil-soluble organic phosphates, organic phosphites, organic phosphonates, organic phosphonites, etc., and their sulfur analogs, the preferred phosphorus-containing antiwear and/or extreme pressure agents for use in this embodiment those which contain both phosphorus and nitrogen.

One such type of phosphorus- and nitrogen-containing antiwear and/or extreme pressure additives which can be employed in the practice of this embodiment of the invention are the phosphorus- and nitrogen-containing compositions of the type described in G.B. 1,009,913; G.B. 1,009,914; U.S. Pat. Nos. 3,197,405 and/or 3,197,496. In general, these compositions are formed by forming an acidic intermediate by the reaction of a hydroxy-substituted triester of a phosphorothioic acid with an inorganic phosphorus acid, phosphorus oxide or phosphorus halide, and neutralizing a substantial portion of said acidic intermediate with an amine or hydroxy-substituted amine.

Another type of phosphorus- and nitrogen-containing antiwear and/or extreme pressure additive which can be used in the compositions of this invention is the amine salts of hydroxy-substituted phosphetanes or the amine salts of hydroxy-substituted thiophosphetanes. Typically, such salts are derived from compounds of the formula

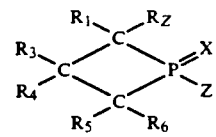

wherein each of $R_1$, $R_2$, $R_3$, $R_4$, $R_5$ and $R_6$ is a hydrogen atom or a carbon-bonded organic group such as a hydrocarbyl group or a substituted hydrocarbyl group wherein the substituent(s) do(es) not materially detract from the predominantly hydrocarbonaceous character of the hydrocarbyl group; X is a sulfur or an oxygen atom and Z is a hydroxyl group or an organic group having one or more acidic hydroxyl groups. Examples of this general type of antiwear and/or extreme pressure agent include the amine salts hydroxyphosphetanes and the amine salts of hydroxy-thiophosphetanes typified by Irgalube 295 additive (Ciba-Geigy Corporation).

Another useful category of phosphorus- and nitrogen-containing antiwear and/or extreme pressure agents is comprised of the amine salts of partial esters of phosphoric and thiophosphoric acids. Such compounds may be collectively represented by the formulas VIII, IX, and X as follows:

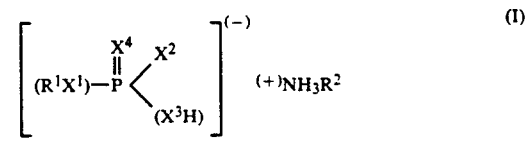

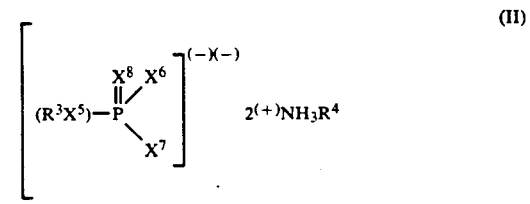

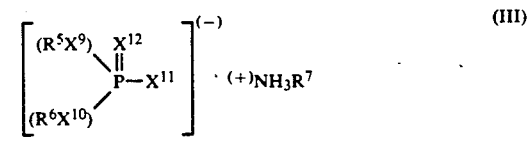

or mixtures thereof. In Formulas VIII, IX and X, each of $R^1$, $R^2$, $R^3$, $R^4$, $R^5$, $R^6$, and $R^7$ is, independently, a hydrocarbyl group and each of $X^1$, $X^2$, $X^3$, $X^4$, $X^5$, $X^6$, $X^7$, $X^8$, $X^9$, $X^{10}$, $X^{11}$, and $X^{12}$ is, independently, an oxygen atom or a sulfur atom.

In one preferred sub-category the amine salts are formed with one or more partially esterified monothiophosphoric acids. These are compounds of Formulas VIII, IX, and X above wherein only one of $X^1$, $X^2$, $X^3$, and $X^4$, only one of $X^5$, $X^6$, $X^7$, and $X^8$, and only one of $X^9$, $X^{10}$, $X^{11}$, and $X^{12}$ is a sulfur atom.

In another preferred sub-category the amine salts are formed with one or more partially esterified phosphoric acids. These are compounds of Formulas VIII, IX, and X above wherein all of $X^1$, $X^2$, $X^3$, $X^4$, $X^5$, $X^6$, $X^7$, $X^8$, $X^9$, $X^{10}$, $X^{11}$, and $X^{12}$ are oxygen atoms.

Another preferred sub-category of amine salts are those formed with one or more partially esterified dithiophosphoric acids. These are compounds of Formulas VIII, IX, and X above wherein two of $X^1$, $X^2$, $X^3$, and $X^4$, two of $X^5$, $X^6$, $X^7$ and $X^8$, and two of $X^9$, $X^{10}$, $X^{11}$, and $X^{12}$ are sulfur atoms.

Also useful are amine salts of Formulas VIII, IX, and X above wherein three or four of $X^1$, $X^2$, $X^3$, and $X^4$, three or four of $X^5$, $X^6$, $X^7$, and $X^8$, and three or four of $X^9$, $X^{10}$, $X^{11}$, and $X^{12}$ are sulfur atoms.

While all of the above oil-soluble amine salts are suitable for use as component 3), it is most preferred to use at least one oil-soluble amine salt of a dihydrocarbyl monothiophosphoric acid (one sulfur atom per molecule), either alone or in combination with at least one oil-soluble amine salt of a dihydrocarbyl phosphoric acid (no sulfur atom in the molecule).

Suitable salts or amine adducts of the partially esterified monothiophosphoric acids include such compounds as:

Octylamine salt of O-monobutylthiophosphoric acid
Octylamine salt of S-monobutylthiophosphoric acid
Octylamine salt of O-monobutylthionophosphoric acid
Octylamine salt of O,O-dibutylthiophosphoric acid
Octylamine salt of O,S-dibutylthiophosphoric acid
Octylamine salt of O,O-dibutylthionophosphoric acid
Octylamine salt of O-monoisobutylthiophosphoric acid
Octylamine salt of S-monoisobutylthiophosphoric acid
Octylamine salt of O-monoisobutylthionophosphoric acid
Octylamine salt of O,O-diisobutylthiophosphoric acid
Octylamine salt of O,S-diisobutylthiophosphoric acid
Octylamine salt of O,O-diisobutylthionophosphoric acid
Octylamine salt of O-monoamylthiophosphoric acid
Octylamine salt of S-monoamylthiophosphoric acid
Octylamine salt of O-monoamylthionophosphoric acid
Octylamine salt of O,O-diamylthiophosphoric acid
Octylamine salt of O,S-diamylthiophosphoric acid
Octylamine salt of O,O-diamylthionophosphoric acid
Octylamine salt of O-monohexylthiophosphoric acid
Octylamine salt of S-monohexylthiophosphoric acid
Octylamine salt of O-monohexylthionophosphoric acid
Octylamine salt of O,O-dihexylthiophosphoric acid
Octylamine salt of O,S-dihexylthiophosphoric acid
Octylamine salt of O,O-dihexylthionophosphoric acid
Octylamine salt of O-monoheptylthiophosphoric acid
Octylamine salt of S-monoheptylthiophosphoric acid
Octylamine salt of O-monoheptylthionophosphoric acid
Octylamine salt of O,O-diheptylthiophosphoric acid
Octylamine salt of O,S-diheptylthiophosphoric acid
Octylamine salt of O,O-diheptylthionophosphoric acid
Octylamine salt of O-mono-2-ethylhexylthiophosphoric acid
Octylamine salt of S-mono-2-ethylhexylthiophosphoric acid
Octylamine salt of O-mono-2-ethylhexylthionophosphoric acid
Octylamine salt of O,O-di-2-ethylhexylthiophosphoric acid
Octylamine salt of O,S-di-2-ethylhexylthiophosphoric acid
Octylamine salt of O,O-di-2-ethylhexylthionophosphoric acid
Octylamine salt of O-monooctylthiophosphoric acid
Octylamine salt of S-monooctylthiophosphoric acid
Octylamine salt of O-monooctylthionophosphoric acid
Octylamine salt of O,O-dioctylthiophosphoric acid
Octylamine salt of O,S-dioctylthiophosphoric acid
Octylamine salt of O,O-dioctylthionophosphoric acid
Octylamine salt of O-mononoylthiophosphoric acid
Octylamine salt of S-mononoylthiophosphoric acid
Octylamine salt of O-mononoylthionophosphoric acid
Octylamine salt of O,O-dinonylthiophosphoric acid
Octylamine salt of O,S-dinonylthiophosphoric acid
Octylamine salt of O,O-dinonylthionophosphoric acid
Octylamine salt of O-monodecylthiophosphoric acid
Octylamine salt of S-monodecylthiophosphoric acid
Octylamine salt of O-monodecylthionophosphoric acid
Octylamine salt of O,O-didecylthiophosphoric acid
Octylamine salt of O,S-didecylthiophosphoric acid
Octylamine salt of O,O-didecylthionophosphoric acid
Octylamine salt of O-monododecylthiophosphoric acid
Octylamine salt of S-monododecylthiophosphoric acid
Octylamine salt of O-monododecylthionophosphoric acid
Octylamine salt of O,O-didodecylthiophosphoric acid
Octylamine salt of O,S-didodecylthiophosphoric acid
Octylamine salt of O,O-didodecylthionophosphoric acid
Octylamine salt of O-monotridecylthiophosphoric acid
Octylamine salt of S-monotridecylthiophosphoric acid
Octylamine salt of O-monotridecylthionophosphoric acid
Octylamine salt of O,O-ditridecylthiophosphoric acid
Octylamine salt of O,S-ditridecylthiophosphoric acid
Octylamine salt of O,O-ditridecylthionophosphoric acid
Octylamine salt of O-monotetradecylthiophosphoric acid
Octylamine salt of S-monotetradecylthiophosphoric acid
Octylamine salt of O-monotetradecylthionophosphoric acid
Octylamine salt of O,O-ditetradecylthiophosphoric acid
Octylamine salt of O,S-ditetradecylthiophosphoric acid
Octylamine salt of O,O-ditetradecylthionophosphoric acid
Octylamine salt of O-monohexadecylthiophosphoric acid
Octylamine salt of S-monohexadecylthiophosphoric acid
Octylamine salt of O-monohexadecylthionophosphoric acid
Octylamine salt of O,O-dihexadecylthiophosphoric acid
Octylamine salt of O,S-dihexadecylthiophosphoric acid
Octylamine salt of O,O-dihexadecylthionophosphoric acid
Octylamine salt of O-monooctadecylthiophosphoric acid
Octylamine salt of S-monooctadecylthiophosphoric acid
Octylamine salt of O-monooctadecylthionophosphoric acid
Octylamine salt of O,O-dioctadecylthiophosphoric acid
Octylamine salt of O,S-dioctadecylthiophosphoric acid
Octylamine salt of O,O-dioctadecylthionophosphoric acid
Octylamine salt of O-monooleylthiophosphoric acid
Octylamine salt of S-monooleylthiophosphoric acid
Octylamine salt of O-monooleylthionophosphoric acid
Octylamine salt of O,O-dioleylthiophosphoric acid
Octylamine salt of O,S-dioleylthiophosphoric acid
Octylamine salt of O,O-dioleylthionophosphoric acid
Octylamine salt of O-monobenzylthiophosphoric acid
Octylamine salt of S-monobenzylthiophosphoric acid Octylamine salt of O-monobenzylthionophosphoric acid
Octylamine salt of O,O-dibenzylthiophosphoric acid
Octylamine salt of O,S-dibenzylthiophosphoric acid
Octylamine salt of O,O-dibenzylthionophosphoric acid
Octylamine salt of O-monocyclohexylthiophosphoric acid
Octylamine salt of S-monocyclohexylthiophosphoric acid
Octylamine salt of O-monocyclohexylthionophosphoric acid
Octylamine salt of O,O-dicyclohexylthiophosphoric acid
Octylamine salt of O,S-dicyclohexylthiophosphoric acid
Octylamine salt of O,O-dicyclohexylthionophosphoric acid
Octylamine salt of O-mono-p-tolylthiophosphoric acid
Octylamine salt of S-mono-p-tolylthiophosphoric acid
Octylamine salt of O-mono-p-tolylthionophosphoric acid
Octylamine salt of O,O-di-p-tolylthiophosphoric acid
Octylamine salt of O,S-di-p-tolylthiophosphoric acid
Octylamine salt of O,O-di-p-tolylthionophosphoric acid
Octylamine salt of O-monoxylylthiophosphoric acid
Octylamine salt of S-monoxylylthiophosphoric acid
Octylamine salt of O-monoxylylthionophosphoric acid
Octylamine salt of O,O-dixylylthiophosphoric acid
Octylamine salt of O,S-dixylylthiophosphoric acid
Octylamine salt of O,O-dixylylthionophosphoric acid
Octylamine salt of O-isopropyl-O-octadecylthiophosphoric acid
Octylamine salt of O-nonyl-S-butylthiophosphoric acid
Octylamine salt of O-undecyl-O-methylthionophosphoric acid
Octylamine salt of O-cyclohexyl-S-decylthiophosphoric acid
Octylamine salt of O-phenyl-S-tetradecylthiophosphoric acid
Octylamine salt of O-pentadecyl-O-cyclohexenylthionophosphoric acid
Octylamine salt of O-ethyl-O-(p-tert-amylphenyl)thionophosphoric acid
Octylamine salt of O-benzyl-S-isononylthiophosphoric acid
Octylamine salt of O-cyclopentyl-O-heptadecylthionophosphoric acid
Octylamine salt of O-oleyl-S-butylthiophosphoric acid
Octylamine salt of O-2-ethylhexyl-O-isooctylthionophosphoric acid
Octylamine salt of O -allyl-S-tridecylthiophosphoric acid.

It will be noted that in the above listing of illustrative amine salts, the partially esterified monothiophosphoric acids have been named, for convenience, by use of the "thio-thiono" system of nomenclature in which thiono refers to a sulfur atom bonded to the phosphorus atom by a double bond whereas thio refers to a sulfur atom that is bonded to the phosphorus atom by a single bond. Such compounds can also be named by use of a "thioic" system of nomenclature. For example, O,O-dihydrocarbylthionophosphoric acid is also known as O,O-dihydrocarbylphosphorothioic acid, (RO)$_2$P(S)(OH). However, except when referring to specific compounds (as in the above "thio-thiono" listing) the term "monothiophosphoric acid" is used generically herein to refer to phosphoric acid having only one sulfur atom, and that sulfur atom can be bonded to the phosphorus atom either by a single bond or by a double bond. Likewise except when referring to specific compounds, the term "dithiophosphoric acid" refers to phosphoric acid having two sulfur atoms both of which can be bonded to the phosphorus atom by single bonds, or one of which is bonded to the phosphorus atom by a double bond and the other of which is bonded to the phosphorus atom by single bond. The same applies to the term "trithiophosphoric acid", wherein two of the three sulfur atoms can be bonded to the phosphorus atom by single bonds and the third by either a single or double bond.

Illustrative examples of amine salts of partial esters of phosphoric acid include the following:
Octylamine salt of monobutylphosphoric acid
Octylamine salt of dibutylphosphoric acid
Octylamine salt of monoisobutylphosphoric acid
Octylamine salt of diisobutylphosphoric acid
Octylamine salt of monoamylphosphoric acid
Octylamine salt of diamylphosphoric acid
Octylamine salt of monohexylphosphoric acid
Octylamine salt of dihexylphosphoric acid
Octylamine salt of monoheptylphosphoric acid
Octylamine salt of diheptylphosphoric acid
Octylamine salt of mono-2-ethylhexylphosphoric acid
Octylamine salt of di-2-ethylhexylphosphoric acid
Octylamine salt of monooctylphosphoric acid
Octylamine salt of dioctylphosphoric acid
Octylamine salt of mononoylphosphoric acid
Octylamine salt of dinonylphosphoric acid
Octylamine salt of monodecylphosphoric acid
Octylamine salt of didecylphosphoric acid
Octylamine salt of monododecylphosphoric acid
Octylamine salt of didodecylphosphoric acid
Octylamine salt of monotridecylphosphoric acid
Octylamine salt of ditridecylphosphoric acid
Octylamine salt of monotetradecylphosphoric acid
Octylamine salt of ditetradecylphosphoric acid
Octylamine salt of monohexadecylphosphoric acid
Octylamine salt of dihexadecylphosphoric acid
Octylamine salt of monooctadecylphosphoric acid
Octylamine salt of dioctadecylphosphoric acid
Octylamine salt of monooleylphosphoric acid
Octylamine salt of dioleylphosphoric acid
Octylamine salt of monobenzylphosphoric acid
Octylamine salt of dibenzylphosphoric acid
Octylamine salt of monocyclohexylphosphoric acid
Octylamine salt of dicyclohexylphosphoric acid
Octylamine salt of mono-p-tolylphosphoric acid
Octylamine salt of di-p-tolylphosphoric acid
Octylamine salt of monoxylylphosphoric acid
Octylamine salt of dixylylphosphoric acid
Octylamine salt of monoisopropyl-monooctadecylphosphoric acid
Octylamine salt of mononyl-monobutylphosphoric acid
Octylamine salt of monoundecyl-monomethylphosphoric acid
Octylamine salt of monocyclohexyl-monodecylphosphoric acid
Octylamine salt of monophenyl-monotetradecylphosphoric acid
Octylamine salt of monopentadecyl-monocyclohexenylphosphoric acid
Octylamine salt of monoethyl-mono(p-tert-amylphenyl)phosphoric acid
Octylamine salt of monobenzyl-monoisononylphosphoric acid Octylamine salt of monocyclopentyl-monoheptadecyl-phosphoric acid Octylamine salt of monooleyl-monobutylphosphoric acid Octylamine salt of mono-(2-ethylhexyl)-monoisooctyl-phosphoric acid Octylamine salt of monoallyl-monotridecylphosphoric acid.

Examples of corresponding amine salts of partially esterified dithiophosphoric acid, of partially esterified trithiophosphoric acid, and of partially esterified tetrathiophosphoric acid will be readily apparent from the above listings.

Octylamine salts or adducts have been set forth in the above two listings merely for purposes of illustration. In lieu of octyl amine salts, or in addition thereto, use can be made of nonylamine, decylamine, undecylamine, dodecylamine, tridecylamine, tetradecylamine, pentadecylamine, hexadecylamine, heptadecylamine, octadecylamine, cyclohexylamine, phenylamine, mesitylamine, oleylamine, cocoamine, soyamine, $C_8$ tertiary alkyl primary amine, $C_{12-14}$ tertiary alkyl primary amine, $C_{22-24}$ tertiary alkyl primary amine, phenethylamine, etc., salts or adducts of partially esterified phosphoric, monothiophosphoric, dithiophosphoric, trithiophosphoric, and/or tetrathiophosphoric acids, including mixtures of any such compounds. Generally speaking, the preferred amine salts are salts of aliphatic amines, especially the saturated or olefinically unsaturated aliphatic primary amines, such as n-octylamine, 2-ethylhexylamine, tert-octylamine, n-decylamine, the $C_{10}$, $C_{12}$, $C_{14}$ and $C_{16}$ tertiary alkyl primary amines (either singly or in any combinations thereof, such as a mixture of the $C_{12}$ and $C_{14}$ tertiary alkyl primary amines), n-undecylamine, a mixture of $C_{14}$ to $C_{18}$ tertiary alkyl primary amines, lauryl amine, hexadecylamine, heptadecylamine, octadecylamine, the $C_{22}$ and $C_{24}$ tertiary alkyl primary amines (either singly or in combination), decenylamine, dodecenylamine, palmitoleylamine, oleylamine, linoleylamine, eicosenylamine, etc. Secondary hydrocarbyl amines and tertiary hydrocarbyl amines can also be used either alone or in combination with each other or in combination with primary amines. Thus any combination of primary, secondary and/or tertiary amines, whether monoamine or polyamine, can be used in forming the salts or adducts.

Similarly, the amines used can be in the form of polyalkylene polyamines; functionally-substituted polyamines such as a succinimide or succinamide of a polyalkylene polyamines such as a polyisobutenyl succinimide of diethylene triamine, a polyisobutenyl succinimide of triethylene tetramine, a polyisobutenyl succinimide of tetraethylene pentamine, a polyisobutenyl succinimide of pentaethylene hexamine (including succinimides made from commercially available polyethylene polyamine mixtures which contain linear, branched and cyclic species); and Mannich bases derived from polyalkylene polyamines of the types just described. Moreover, the polyalkylene polyamines whether in the free state or in the form of a succinimide, succinamide, or Mannich base, can be partially boronated, partially phosphorylated, or partially acylated with a reagent such as maleic anhydride, malic acid, itaconic acid, itaconic anhydride, thiomalic acid, fumaric acid, and the like, provided that such boronated or phosphorylated or acylated amine or amine moiety contains at least sufficient residual basicity to enable it to form a salt with the partially esterified phosphoric or thiophosphoric acid. Alkylene polyamines in the form of succinimides, succinamides or Mannich bases which have been boronated and phosphorylated are described for example in U.S. Pat. No. 4,857,214.

Use of primary amines is preferred. Especially preferred amines are alkyl monoamines and alkenyl monoamines having from about 8 to about 24 carbon atoms in the molecule.

Amines having less than 8 carbon atoms can be used, including methyl amine, etc., provided the resultant amine salt is oil-soluble. Likewise, amines having more than 24 carbon atoms can be used, again with the proviso that the resultant amine salt is oil soluble.

Methods for the preparation of such amine salts are well known and reported in the literature. See for example, U.S. Pat. Nos. 2,063,629; 2,224,695; 2,447,288; 2,616,905; 3,984,448; 4,431,552; Pesin et al, *Zhurnal Obshchei Khimii*, Vol. 31, No. 8, pp. 2508-2515 (1961); and International Application Publication No. WO 87/07638.

It should be noted that amine salts of partially esterified monothiophosphoric acids are usually made by reacting a mono- and/or dihydrocarbyl phosphite with sulfur or an active sulfur-containing compound such as are referred to above under the caption "Sulfur-Containing Antiwear and/or Extreme Pressure Agents" and one or more primary or secondary amines. Such reactions tend to be highly exothermic reactions which can become uncontrollable, if not conducted properly. One preferred method of forming these amine salts involves a process which comprises (i) introducing, at a rate such that the temperature does not exceed about 60° C., one or more dihydrocarbyl hydrogen phosphites, such as a dialkyl hydrogen phosphite, into an excess quantity of one or more active sulfur-containing materials, such as sulfurized branched-chain olefin (e.g., isobutylene, diisobutylene, triisobutylene, etc.), while agitating the mixture so formed, (ii) introducing into this mixture, at a rate such that the temperature does not exceed about 60° C., one or more aliphatic primary or secondary amines, preferably one or more aliphatic primary monoamines having in the range of about 8 to about 24 carbon atoms per molecule while agitating the mixture so formed, and (iii) maintaining the temperature of the resultant agitated reaction mixture at between about 55° and about 60° C. until reaction is substantially complete. Another suitable way of producing these amine salts is to concurrently introduce all three of the reactants into the reaction zone at suitable rates and under temperature control such that the temperature does not exceed about 60° C. Another preferred way of forming amine salts of partially esterified monothiophosphoric acids is to pre-react elemental sulfur with the amine for a short period of time and then add thereto the appropriate dihydrocarbyl hydrogen phosphite at a rate such that the temperature does not become excessive and the reaction uncontrollable.

As indicated above, the amine salts of dihydrocarbyl esters of thiophosphoric acids are comprised of the oil-soluble amine salts (preferably the aliphatic monoamine salts) of one or more dihydrocarbyl esters of a thiophosphoric acid, which esters can be derived from a tetrathiophosphoric acid, a trithiophosphoric acid, a dithiophosphoric acid, or a monothiophosphoric acid, or a mixture of any two or more of the foregoing. The amine salts of dihydrocarbyl esters of a dithiophosphoric acid are preferred, and the amine salts of dihydrocarbyl esters of a monothiophosphoric acid are particularly preferred.

As pointed out above, oil-soluble phosphorus- and nitrogen-containing compounds are the preferred antiwear and/or extreme pressure agents for use in the compositions of this invention. However, metal-free phosphorus-containing compounds which do not contain nitrogen can be used either in lieu of or in addition to the phosphorus- and nitrogen-containing antiwear and/or extreme pressure agents described above. Such nitrogen-free compounds are for the most part partially or fully esterified acids of phosphorus, and include for example oil-soluble phosphates, phosphites, phosphonates, phosphonites, and their various sulfur analogs. Examples include monohydrocarbyl phosphites; monohydrocarbyl phosphates; monohydrocarbyl mono-, di-, and trithiophosphites; monohydrocarbyl mono-, di-, tri-, and tetrathiophosphates; dihydrocarbyl phosphites; dihydrocarbyl phosphates; dihydrocarbyl mono-, di-, and trithiophosphites; dihydrocarbyl mono-, di-, tri-, and tetrathiophosphates; trihydrocarbyl phosphites; trihydrocarbylphosphates; trihydrocarbyl mono-, di-, and trithiophosphites; trihydrocarbyl mono-, di-, tri-, and tetrathiophosphates; the various hydrocarbyl phosphonates and thiophosphonates; the various hydrocarbyl phosphonites and thiophosphonites, and analogous oil-soluble derivatives of polyphosphoric and polythiophosphoric acids; and many others. A few specific examples of such compounds are tributyl phosphate, tri-(2-ethylhexyl) phosphate, trioleyl phosphate, tris(2-chloroethyl) phosphate, tricyclohexyl phosphate, triphenyl phosphate, tricresyl phosphate, cresyl diphenyl phosphate, triethyl phosphite, tributyl phosphite, tris(2-butoxyethyl) phosphite, trioctyl phosphite, tris(tridecyl) phosphite, trilauryl phosphite, triphenyl phosphite, tricresyl phosphite, the mono- or diamyl hydrogen phosphates or mixtures thereof, the mono- or di-2-ethyl-1-hexyl hydrogen phosphates or mixtures thereof, dibutyl hydrogen phosphite, bis(tridecyl) hydrogen phosphite, the diisooctyl ester of butylphosphonic acid, the dihexyl ester of decylphosphonic acid, sulfur-containing analogs of each of the foregoing, dihexyl thiophosphite, diisopropyl dithiophosphate, tris(tridecyl)tetrathiophosphate, and like compounds. Also useful are the oil-soluble heterocyclic phosphorus compounds such as the phosphetanes and thiophosphetanes and their derivatives, such as are described for example in U.S. Pat. Nos. 3,891,726; 3,975,465; *Journal of The Chemical Society, Dalton Transactions*, 1973, pages 1576–1582; 2641–2646; 2701–2707; and Ibid, 1974. pages 633–638.

When including component 3) in the practice of Embodiment D, use can be made of any of the oil-soluble and/or oil-dispersible sulfur-containing antiwear and/or extreme pressure agents referred to hereinabove with reference to Embodiment C.

The lubricating oil compositions and addtive concentrates of this invention, including the compositions of Embodiments A), B), C), and D) can, and in most cases will, contain still additional components, such as one or more of the following:

Amine Salts of Carboxylic Acids

One or more amine salts of one or more long chain carboxylic acids can be used in such compositions. At suitably high concentrations such amine salts improve the performance of sulfur-containing antiwear and/or extreme pressure agents when operating under highly stressful servive conditions.

The acids of the amine salts can be monocarboxylic acids or polycarboxylic acids. Generally speaking, these acids contain from about 8 to about 50 carbon atoms in the molecule and thus the salts are oil-soluble. A variety of amines can be used in forming such salts, including primary, secondary and tertiary amines, and the amines can be monoamines, or polyamines. Further, the amines may be cyclic or acyclic aliphatic amines, aromatic amines, heterocyclic amines, or amines containing various mixtures of acyclic and cyclic groups.

Preferred amine salts include the alkyl and alkenyl amine salts of alkanoic acids and/or alkenoic acids, the alkyl and alkenyl amine salts of alkanedioic acids and/or alkenedioic acids and any combination of the foregoing.

The amine salts are formed by classical chemical reactions, namely, the reaction of an amine or mixture of amines, with the appropriate acid or mixture of acids. Accordingly, further discussion concerning methods for the preparation of such materials would be redundant.

Among the amine salts of long-chain acids that may be used are the following: the octyl amine salt of $C_{36}$ dimer acid (made by dimerization of linoleic acid), lauryl ammonium lau-rate (i.e. the lauryl amine salt of lauric acid), stearyl ammonium laurate, cyclohexyl ammonium laurate, octyl ammonium laurate, pyridine laurate, aniline laurate, lauryl ammonium stearate, stearyl ammonium stearate, cyclohexyl ammonium stearate, octylammonium stearate, pyridine stearate, aniline stearate, lauryl ammonium octanoate, stearyl ammonium octanoate, cyclohexyl ammonium octanoate, octyl ammonium octanoate, pyridine octanoate, aniline octanoate, nonyl ammonium laurate, nonyl ammonium stearate, nonyl ammonium octanoate, lauryl ammonium nonanoate, stearyl ammonium nonanoate, cyclohexyl ammonium nonanoate, octyl ammonium nonanoate, pyridine nonanoate, aniline nonanoate, nonyl ammonium nonanoate, lauryl ammonium decanoate, stearyl ammonium decanoate, cyclohexyl ammonium decanoate, octyl ammonium decanoate, pyridine decanoate, aniline decanoate, decyl ammonium laurate, decyl ammonium stearate, decyl ammonium octanoate, decyl ammonium nonanoate, decyl ammonium decanoate, bis octyl amine salt of suberic acid, bis cyclohexyl amine salt of suberic acid, bis lauryl amine salt of suberic acid, bis stearyl amine salt of suberic acid, bis octyl amine salt of sebacic acid, bis cyclohexyl amine salt of sebacic acid, bis lauryl amine salt of sebacic acid, bis stearyl amine salt of sebacic acid, the tert-dodecyl and tert-tetradecyl primary amine salts of octanoic acid, the tert-decyl and tert-dodecyl primary amine salts of octanoic acid, the tert-dodecyl and tert- tetradecyl primary amine salts of lauric acid, the tert-decyl and tert-dodecyl primary amine salts of lauric acid, the tert- dodecyl and tert-tetradecyl primary amine salts of stearic acid, the tert-decyl and tert-dodecyl primary amine salts of stearic acid, the hexyl amine salt of $C_{24}$-dicarboxylic acid, the octyl amine salt of $C_{28}$-dicarboxylic acid, the octyl amine salt of $C_{30}$-dicarboxylic acid, the decyl amine salt of $C_{30}$-dicarboxylic acid, the octyl amine salt of $C_{32}$-dicarboxylic acid, the bis lauryl dimethyl amine salt of traumatic acid, diethyl ammonium laurate, dioctyl ammonium laurate, dicyclohexyl ammonium laurate, diethyl ammonium octanoate, dioctyl ammonium octanoate, dicyclohexyl ammonium octanoate, diethyl ammonium stearate, dioctyl ammonium stearate, diethyl ammonium stearate, dibutyl ammonium stearate, dicyclopentyl ammonium stearate, dipropyl ammonium benzoate, didecyl ammonium benzoate, dimethylcyclohexyl ammonium benzoate, triethyl ammonium laurate, triethyl ammonium octanoate, triethyl ammonium stearate, triethyl ammonium benzoate, trioctyl ammonium laurate, trioctyl ammonium octanoate, trioctyl ammonium stearate, trioctyl ammonium benzoate, and the like. It will be understood of course that the amine salt of the monocarboxylic and/or polycarboxylic acid used should be sufficiently soluble in the base oil used as to provide homogeneous solution at the concentration employed.

Among the preferred amine salts for use in accordance with this invention are the primary amine salts of long chain monocarboxylic acids in which the amine thereof is a monoalkyl monoamine, $RNH_2$; the secondary amine salts of long chain monocarboxylic acids in which the amine thereof is a dialkyl monoamine, $R_2NH$; the tertiary amine salts of long chain monocarboxylic acids in which the amine thereof is a trialkyl monoamine, $R_3N$; the bis primary amine salts of long chain dicarboxylic acids in which the amine thereof is a monoalkyl monoamine, $RNH_2$; the bis secondary amine salts of long chain dicarboxylic acids in which the amine thereof is a dialkyl monoamine, $R_2NH$; the bis tertiary amine salts of long chain dicarboxylic acids in which the amine thereof is a trialkyl monoamine, $R_3N$; and mixtures thereof. In the foregoing formulae, R is an alkyl group which contains up to about 30 or more carbon atoms, and preferably from about 6 to about 24 carbon atoms.

Demulsifiers

Typical additives which may be employed as demulsifiers include alkyl benzene sulphonates, polyethylene oxides, polypropylene oxides, block copolymers of ethylene oxide and propylene oxide, salts and esters or oil soluble acids, and the like.

Thus, for example use can be made of oxyalkylated trimethylol alkanes with molecular weights in the range of 1,000 to 10,000, and preferably in the range of 3,000 to 8,000. Preferably, the oxyalkylated trimethylol alkane is an oxyalkylated trimethylol ethane or propane, especially where the oxyalkylene groups are composed of a mixture of propyleneoxy and ethylenoxy groups and where these groups are so disposed as to form relatively hydrophobic blocks adjacent the trimethylol group and relatively hydrophilic blocks remote the trimethylol group. Typical oxyalkylated trimethylol propane demulsifiers are described in U.S. Pat. No. 3,101,374. Commercially available products of this type are available from BASF Corporation under the Pluradot trademark. They are available in various molecular weights. Pluradot HA-510 has an average molecular weight of 4,600 and Pluradot HA-530 has an average molecular weight of about 5,300. Pluradot additives are propoxylated and ethoxylated trimethylol propanes.

Another type of suitable demulsifers are oxyalkylated alkyl phenol-formaldehyde condensation products. Typically, these products have molecular weights in the range of about 4,000 to about 6,000 and are comprised of lower alkyl substituted phenol moieties joined together by methylene groups and in which the hydroxyl groups of the phenolic moieties have been ethoxylated. One such commercial product is marketed by Ceca S.A. of Paris, France under the "Prochinor GR77" trade name. The product is supplied as a concentrate in an aromatic solvent and the active ingredient is believed to be an ethoxylated nonylphenol-formaldehyde condensate of molecular weight 4,200 (by gel permeation chromatography calibrated with polystyrene).

Another suitable type of demulsifier is comprised of the tetra-polyoxyalkylene derivatives of ethylene diamine, especially the tetra-poly(oxyethylene)-poly(oxypropylene) derivatives of ethylene diamine. Materials of this type are available commercially from BASF Corporation under the "Tetronics" trademark. Materials of this general type are described in U.S. Pat. No. 2,979,528.

Mixtures of alkylaryl sulphonates, polyoxyalkylene glycols and oxyalkylated alkylphenolic resins, such as are available commercially from Petrolite Corporation under the TOLAD trademark, are also suitable. One such proprietary product, identified as TOLAD 286K, is understood to be a mixture of these components dissolved in a solvent composed of alkyl benzenes. TOLAD 286 is believed to be a similar product wherein the solvent is composed of a mixture of heavy aromatic naphtha and isopropyl alcohol.

Other preferred demulsifiers are proprietary materials available from BASF Corporation under the Pluronic trademark. These are block copolymers of propylene oxide and ethylene oxide.

Copper Corrosion Inhibitors

One type of such additives is comprised of thiazoles, triazoles and thiadiazoles. Examples of such compounds include benzotriazole, tolyltriazole, octyltriazole, decyltriazole, dodecyltriazole, 2-mercaptobenzothiazole, 2,5-dimercapto-1,3,4-thiadiazole, 2-mercapto-5-hydrocarbylthio-1,3,4-thiadiazoles, 2-mercapto-5-hydrocarbyldithio-1,3,4-thiadiazoles, 2,5-bis(hydrocarbylthio)-1,3,4-thiadiazoles, and 2,5-bis(hydrocarbyldithio)-1,3,4-thiadiazoles. The preferred compounds are the 1,3,4-thiadiazoles, especially the 2-hydrocarbyldithio-5-mercapto-1,3,4-dithiadiazoles and the 2,5-bis(hydrocarbyldithio)-1,3,4-thiadiazoles, a number of which are available as articles of commerce. Such compounds are generally synthesized from hydrazine and carbon disulfide by known procedures. See for example U.S. Pat. Nos. 2,749,311; 2,760,933; 2,765,289; 2,85°,453; 2,910,439; 3,663,561; 3,862,798; 3,840,549; and 4,097,387.

Other suitable inhibitors of copper corrosion include ether amines; polyethoxylated compounds such as ethoxylated amines, ethoxylated phenols, and ethoxylated alcohols; imidazolines; and the like. Materials of these types are well known to those skilled in the art and a number of such materials are available as articles of commerce.

Supplemental Ashless Dispersants

Any of a variety of additional ashless dispersants can be utilized in the compositions of this invention. These include carboxylic ashless dispersants, Mannich base dispersants, polymeric polyamine dispersants, and post-treated dispersants of these types.

The carboxylic ashless dispersants are reaction products of an acylating agent (e.g., a monocarboxylic acid, dicarboxylic acid or other polycarboxylic acid, or derivatives thereof) with one or more polyamines and/or polyhydroxy compounds. These products, are described in many patents, including British Patent Specification 1,306,529 and the following U.S. Pat. Nos.:

3,163,603; 3,184,474; 3,215,707; 3,219,666; 3,271,310; 3,272,746; 3,281,357; 3,306,908; 3,311,558; 3,316,177; 3,340,281; 3,341,542; 3,346,493; 3,381,022; 3,399,141; 3,415,750; 3,433,744; 3,444,170; 3,448,048; 3,448,049; 3,451,933; 3,454,607; 3,467,668; 3,522,179; 3,541,012; 3,542,678; 3,574,101; 3,576,743; 3,630,904; 3,632,510; 3,632,511; 3,697,428; 3,725,441; 3,868,330; 3,948,800; 4,234,435; and Re. 26,433.

There are a number of sub-categories of carboxylic ashless dispersants. One such sub-category is composed of the polyamine succinamides and more preferably the polyamine succinimides in which the succinic group contains a hydrocarbyl substituent, usually an alkenyl substituent, containing at least 30 carbon atoms. These dispersants are usually formed by reacting a polyamine with an alkenyl succinic acid or anhydride such as a polyisobutenyl succinic acid and anhydride wherein the polyisobutenyl group has a number average molecular weight of 500 to 5,000, preferably 700 to 2,500, more preferably 700 to 1,400, and typically in the range of 800 to 1,300. The polyamine used in forming such compounds contains at least one primary amino group capable of forming an imide group on reaction with a hydrocarbon-substituted succinic acid or acid derivative thereof such an anhydride, lower alkyl ester, acid halide, or acid-ester. The literature is replete with descriptions of polyamines suitable for use in forming such carboxylic ashless dispersants. See for example U.S. Pat. No. 5,034,018 which describes not only simple polyamines but amido-amine adducts which are suitable for use in forming such carboxylic ashless dispersants. Representative examples of such dispersants are given in U.S. Pat. Nos. 3,172,892; 3,202,678; 3,216,936; 3,219,666; 3,254,025; 3,272,746; 4,234,435; and 5,034,018. As used herein the term "succinimide" is meant to encompass the completed reaction product from reaction between the amine reactant(s) and the hydrocarbon-substituted carboxylic acid or anhydride (or like acid derivative) reactant(s), and is intended to encompass compounds wherein the product may have amide, amidine, and/or salt linkages in addition to the imide linkage of the type that results from the reaction of a primary amino group and an anhydride moiety.

Another sub-category of carboxylic ashless dispersants which can be used in the compositions of this invention includes alkenyl succinic acid esters and diesters of alcohols containing 1–20 carbon atoms and 1–6 hydroxyl groups. Representative examples are described in U.S. Pat. Nos. 3,331,776; 3,381,022; and 3,522,179. The alkenyl succinic portion of these esters corresponds to the alkenyl succinic portion of the succinimides described above. Alcohols useful in preparing the esters include methanol, ethanol, 2-methylpropanol, octadecanol, eicosanol, ethylene glycol, diethylene glycol, tetraethylene glycol, diethylene glycol monoethylether, propylene glycol, tripropylene glycol, glycerol, sorbitol, 1,1,1-trimethylol ethane, 1,1,1-trimethylol propane, 1,1,1-trimethylol butane, pentaerythritol, dipentaerythritol, and the like.

The succinic esters are readily made by merely heating a mixture of alkenyl succinic acid, anhydrides or lower alkyl (e.g., $C_1$–$C_4$) ester with the alcohol while distilling out water or lower alkanol. In the case of acid-esters less alcohol is used. In fact, acid-esters made from alkenyl succinic anhydrides do not evolve water. In another method the alkenyl succinic acid or anhydrides can be merely reacted with an appropriate alkylene oxide such as ethylene oxide, propylene oxide, and the like, including mixtures thereof.

Still another sub-category of carboxylic ashless dispersants useful in forming compositions of this invention comprises an alkenyl succinic ester-amide mixture. These may be made by heating the above-described alkenyl succinic acids, anhydrides or lower alkyl esters or etc. with an alcohol and an amine either sequentially or in a mixture. The alcohols and amines described above are also useful in this embodiment. Alternatively, amino alcohols can be used alone or with the alcohol and/or amine to form the ester-amide mixtures. The amino alcohol can contain 1–20 carbon atoms, 1–6 hydroxy groups and 1–4 amine nitrogen atoms. Examples are ethanolamine, diethanolamine, N-ethanol-diethylene triamine, and trimethylol aminomethane. Representative examples of suitable ester-amide mixtures are referred to in U.S. Pat. Nos. 3,184,474; 3,576,743; 3,632,511; 3,804,763; 3,836,471; 3,862,981; 3,936,480; 3,948,800; 3,950,341; 3,957,854; 3,957,855; 3,991,098; 4,071,548; and 4,173,540.

As in the case of the other supplemental carboxylic ashless dispersants discussed above, the alkenyl succinic anhydride or like acylating agent is derived from a polyolefin, preferably a polyisobutene, having a number average molecular weight of 500 to 5,000, preferably 700 to 2,500, more preferably 700 to 1,400, and especially 800 to 1,200. Likewise, residual unsaturation in the polyalkenyl substituent group can be used as a reaction site as for example, by hydrogenation, sulfurization, or the like.

The polymeric polyamine dispersants are polymers containing basic amine groups and oil solubilizing groups (for example, pendant alkyl groups having at least about 8 carbon atoms). Such materials include, but are not limited to, interpolymers of decyl methacrylate, vinyl decyl ether or a relatively high molecular weight olefin with aminoalkyl acrylates and aminoalkyl acrylamides. Examples of polymeric polyamine dispersants are set forth in the following patents: U.S. Pat. Nos. 3,329,658; 3,449,250; 3,493,520; 3,519,565; 3,666,730; 3,687,849; and 3,702,300.

The various supplemental ashless dispersants referred to above can be subjected to post-treatment with one or more suitable reagents such as are described hereinabove. Examples of post-treatment procedures and post-treated ashless dispersants are set forth in the following U.S. patents: U.S. Pat. Nos. 3,036,003; 3,200,107; 3,216,936; 3,256,185; 3,278,550; 3,312,619; 3,366,569; 3,367,943; 3,373,111; 3,403,102; 3,442,808; 3,455,831; 3,455,832; 3,493,520; 3,502,677; 3,513,093; 3,573,010; 3,579,450; 3,591,598; 3,600,372; 3,639,242; 3,649,229; 3,649,659; 3,702,757; 3,708,522; 4,971,598; and 4,971,711.

Antioxidants

Most oleaginous compositions will contain a conventional quantity of one or more antioxidants in order to protect the composition from premature degradation in the presence of air, especially at elevated temperatures. Typical antioxidants include hindered phenolic antioxidants, secondary aromatic amine antioxidants, sulfurized phenolic antioxidants, oil-soluble copper compounds, phosphorus-containing antioxidants, and the like.

Illustrative sterically hindered phenolic antioxidants include ortho-alkylated phenolic compounds such as 2,6-di-tert-butylphenol, 4-methyl-2,6-di-tert-butylphenol, 2,4,6-tri-tert-butylphenol, 2-tert-butylphenol, 2,6-diisopropylphenol, 2-methyl-6-tert-butylphenol, 2,4-dimethyl-6-tert-butylphenol, 4-(N,N-dimethylaminomethyl)-2,6-di-tert-butylphenol, 4-ethyl-2,6-di-tert-butylphenol, 2-methyl-6-styrylphenol, 2,6-di-styryl-4-nonylphenol, and their analogs and homologs. Mixtures of two or more such mononuclear phenolic compounds are also suitable.

Also useful are methylene-bridged alkylphenols, and these can be used singly or in combinations with each other, or in combinations with sterically-hindered unbridged phenolic compounds. Illustrative methylene bridged compounds include 4,4'-methylenebis(6-tert-butyl-o-cresol), 4,4'-methylenebis(2-tert-amyl-o-cresol), 2,2'-methylenebis(4-methyl-6-tert- butylphenol), 4,4'-methylenebis(2,6-di-tert-butylphenol), and similar compounds. Preferred are mixtures of methylene- bridged alkylphenols such as are described in U.S. Pat. No. 3,211,652.

Amine antioxidants, especially oil-soluble aromatic secondary amines can also be used. Although aromatic secondary monoamines are preferred, aromatic secondary polyamines are also suitable. Illustrative aromatic secondary monoamines include diphenylamine, alkyl diphenylamines containing 1 or 2 alkyl substituents each having up to about 16 carbon atoms, phenyl-$\alpha$-naphthylamine, phenyl-$\beta$-naphthylamine, alkyl- or aralkyl-substituted phenyl-$\alpha$-naphthylamine containing one or two alkyl or aralkyl groups each having up to about 16 carbon atoms, alkyl- or aralkyl-substituted phenyl-$\beta$-naphthylamine containing one or two alkyl or aralkyl groups each having up to about 16 carbon atoms, and similar compounds.

A preferred type of aromatic amine antioxidant is an alkylated diphenylamine of the general formula

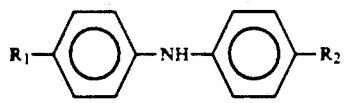

wherein $R_1$ is an alkyl group (preferably a branched alkyl group) having 8 to 12 carbon atoms, (more preferably 8 or 9 carbon atoms) $R_2$ is a hydrogen atom or an alkyl group (preferably a branched alkyl group) having 8 to 12 carbon atoms, (more preferably 8 or 9 carbon atoms). Most preferably, $R_1$ and $R_2$ are the same. One such preferred compound is available commercially as Naugalube 438L, a material which is understood to be predominately a 4,4'-dinonyldiphenylamine (i.e., bis(4-nonylphenyl)amine) wherein the nonyl groups are branched.

Another useful type of antioxidant for inclusion in the compositions of this invention is comprised to one or more liquid, partially sulfurized phenolic compounds such as are prepared by reacting sulfur monochloride with a liquid mixture of phenols—at least about 50 weight percent of which mixture of phenols is composed of one or more reactive, hindered phenols—in proportions to provide from about 0.3 to about 0.7 gram atoms of sulfur monochloride per mole of reactive, hindered phenol so as to produce a liquid product. Typical phenol mixtures useful in making such liquid product compositions include a mixture containing by weight about 75% of 2,6-di-tert-butylphenol, about 10% of 2-tert-butylphenol, about 13% of 2,4,6-tri-tert-butylphenol, and about 2% of 2,4-di-tert-butylphenol. The reaction is exothermic and thus is preferably kept within the range of about 15° C. to about 70° C., most preferably between about 40° C. to about 60° C.

Mixtures of different antioxidants can also be used. One suitable mixture is comprised of a combination of (i) an oil-soluble mixture of at least three different sterically-hindered tertiary butylated monohydric phenols which is in the liquid state at 25° C., (ii) an oil-soluble mixture of at least three different sterically-hindered tertiary butylated methylene-bridged polyphenols, and (iii) at least one bis(4-alkylphenyl)amine wherein the alkyl group is a branched alkyl group having 8 to 12 carbon atoms, the proportions of (i), (ii) and (iii) on a weight basis falling in the range of 3.5 to 5.0 parts of component (i) and 0.9 to 1.2 parts of component (ii) per part by weight of component (iii).

Rust Inhibitors

The compositions of this invention may also contain a suitable quantity of a rust inhibitor. This may be a single compound or a mixture of compounds having the property of inhibiting corrosion of ferrous metal surfaces. Such materials include oil-soluble monocarboxylic acids such as 2-ethylhexanoic acid, lauric acid, myristic acid, palmitic acid, oleic acid, linoleic acid, linolenic acid, behenic acid, cerotic acid, etc., and oil-soluble polycarboxylic acids including dimer and trimer acids, such as are produced from tall oil fatty acids, oleic acid, linoleic acid, or the like. Other suitable corrosion inhibitors include alkenylsuccinic acids in which the alkenyl group contains 10 or more carbon atoms such as, for example, tetrapropenylsuccinic acid, tetradecenylsuccinic acid, hexadecenylsuccinic acid, and the like; long-chain $\alpha\omega$-dicarboxylic acids in the molecular weight range of 600 to 3000; and other similar materials. Products of this type are currently available from various commercial sources, such as, for example, the dimer and trimer acids sold under the HYSTRENE trademark by the Humco Chemical Division of Witco Chemical Corporation and under the EMPOL trademark by Emery Chemicals. Another useful type of acidic corrosion inhibitors are the half esters of alkenyl succinic acids having 8 to 24 carbon atoms in the alkenyl group with alcohols such as the polyglycols. The corresponding half amides of such alkenyl succinic acids are also useful. Although added in acidic form, some or all of the carboxylic groups of these carboxylic acid type corrosion inhibitors may be neutralized by excess amine present in the compositions. Other suitable corrosion inhibitors include ether amines; acid phosphates; amines; polyethoxylated compounds such as ethoxylated amines, ethoxylated phenols, and ethoxylated alcohols; imidazolines; and the like. Materials of these types are well known to those skilled in the art and a number of such materials are available as articles of commerce.

Other useful corrosion inhibitors are aminosuccinic acids or derivatives thereof represented by the formula:

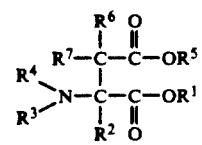

wherein each of $R^1$, $R^2$, $R^5$, $R^6$ and $R^7$ is, independently, a hydrogen atom or a hydrocarbyl group containing 1 to 30 carbon atoms, and wherein each of $R^3$ and $R^4$ is, independently, a hydrogen atom, a hydrocarbyl group containing 1 to 30 carbon atoms, or an acyl group containing from 1 to 30 carbon atoms. The groups $R^1$, $R^2$, $R^3$, $R^4$, $R^5$, $R^6$ and $R^7$, when in the form of hydrocarbyl groups, can be, for example, alkyl, cycloalkyl or aromatic containing groups. Preferably $R^1$ and $R^5$ are the same or different straight-chain or branched-chain hydrocarbon radicals containing 1–20 carbon atoms. Most preferably, $R^1$ and $R^5$ are saturated hydrocarbon radicals containing 3–6 carbon atoms. $R^2$, either $R^3$ or $R^4$, $R^6$ and $R^7$, when in the form of hydrocarbyl groups, are preferably the same or different straight-chain or branched-chain saturated hydrocarbon radicals. Preferably a dialkyl ester of an aminosuccinic acid is used in which $R^1$ and $R^5$ are the same or different alkyl groups containing 3–6 carbon atoms, $R^2$ is a hydrogen atom, and either $R^3$ or $R^4$ is an alkyl group containing 15–20 carbon atoms or an acyl group which is derived from a saturated or unsaturated carboxylic acid containing 2–10 carbon atoms.

Most preferred of the aminosuccinic acid derivatives is a dialkylester of an aminosuccinic acid of the above formula wherein $R^1$ and $R^5$ are isobutyl, $R^2$ is a hydrogen atom, $R^3$ is octadecyl and/or octadecenyl and $R^4$ is 3-carboxy-1-oxo-2-propenyl. In such ester $R^6$ and $R^7$ are most preferably hydrogen atoms.

Antifoam Agents

Suitable antifoam agents include silicones and organic polymers such as acrylate polymers. Various antifoam agents are described in *Foam Control Agents* by H. T. Kerner (Noyes Data Corporation, 1976, pages 125–176). Mixtures of silicone-type antifoam agents such as the liquid dialkyl silicone polymers with various other substances are also effective. Typical of such mixtures are silicones mixed with an acrylate polymer, silicones mixed with one or more amines, and silicones mixed with one or more amine carboxylates. Other such mixtures include combinations of a dimethyl silicone oil with (i) a partial fatty acid ester of a polyhydric alcohol (U.S. Pat. No. 3,235,498); (ii) an alkoxylated partial fatty acid ester of a polyhydric alcohol (U.S. Pat. No. 3,235,499); (iii) a polyalkoxylated aliphatic amine (U.S. Pat. No. 3,235,501); and (iv) an alkoxylated aliphatic acid (U.S. Pat. No. 3,235,502). Also useful are the metal salts of styrene-maleic anhydride copolymers (U.S. Pat. No. 3,296,131).

Friction Modifiers

These materials include such substances as the alkyl phosphonates as disclosed in U.S. Pat. No. 4,356,097, aliphatic hydrocarbyl-substituted succinimides derived from ammonia or alkyl monoamines as disclosed in European Patent Publication No. 20037, dimer acid esters as disclosed in U.S. Pat. No. 4,105,571, oleamide, and the like. Such additives, when used are generally present in amounts of 0.1 to 5 weight percent. Glycerol oleates are another example of fuel economy additives and these are usually present in very small amounts, such as 0.05 to 0.2 weight percent based on the weight of the formulated oil.

Other suitable friction modifiers include aliphatic amines or ethoxylated aliphatic amines, aliphatic fatty acid amides, aliphatic carboxylic acids, aliphatic carboxylic esters, aliphatic carboxylic ester-amides, aliphatic phosphates, aliphatic thiophosphonates, aliphatic thiophosphates, etc., wherein the aliphatic group usually contains above about eight carbon atoms so as to render the compound suitably oil soluble.

A desirable friction modifier additive combination which may be used in the practice of this invention is described in European Patent Publication No. 389,237. This combination involves use of a long chain succinimide derivative and a long chain amide.

Seal Swell Agents

Additives may be introduced into the compositions of this invention in order to improve the seal performance (elastomer compatibility) of the compositions. Known materials of this type include dialkyl diesters such as dioctyl sebacate, aromatic hydrocarbons of suitable viscosity such as Panasol AN-3N, products such as Lubrizol 730, polyol esters such as Emery 2935, 2936, and 2939 esters from the Emery Group of Henkel Corp. and Hatcol 2352, 2962, 2925, 2938, 2939, 2970, 3178, and 4322 polyol esters from Hatco Corp. Generally speaking the most suitable diesters include the adipates, azelates, and sebacates of $C_8$–$C_{13}$ alkanols (or mixtures thereof), and the phthalates of $C_4$–$C_{13}$ alkanols (or mixtures thereof). Mixtures of two or more different types of diesters (e.g., dialkyl adipates and dialkyl azelates, etc.) can also be used. Examples of such materials include the n-octyl, 2-ethylhexyl, isodecyl, and tridecyl diesters of adipic acid, azelaic acid, and sebacic acid, and the n-butyl, isobutyl, pentyl, hexyl, heptyl, octyl, nonyl, decyl, undecyl, dodecyl, and tridecyl diesters of phthalic acid.

Viscosity Index Improvers

Depending upon the viscosity grade required, the lubricant compositions can contain one or more viscosity index improvers (polymeric materials which are often supplied in the form of a solution in a solvent or carrier fluid). Among the numerous types of materials known for such use are hydrocarbon polymers grafted with, for example, nitrogen-containing polymers, olefin polymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl pyrrolidone or dimethylaminoalkyl methacrylate; post-grafted polymers of ethylene-propylene with an active monomer such as maleic anhydride which may be further reacted with an alcohol or an alkylene polyamine; styrene/maleic anhydride polymers post-treated with alcohols and/or amines, and the like.

Dispersant viscosity index improvers, which combine the activity of dispersants and viscosity index improvers, suitable for use in the compositions of this invention are described, for example, in U.S. Pat. Nos. 3,702,300; 4,068,056; 4,068,058; 4,089,794; 4,137,185; 4,146,489; 4,149,984; 4,160,739; 4,519,929; 5,035,819; 5,035,820; 5,035,821; and 5,035,822.

When using a viscosity index improver or a dispersant viscosity index improver it is preferred to use a material which exhibits high shear stability as measured by the FZG or Kurt-Orbahn shear stability rigs. Lubrizol 3174 additive (The Lubrizol Corporation) and HiTEC® 630 additive (Ethyl Petroleum Additives Ltd.; Ethyl Petroleum Additives Inc.; Ethyl S.A.; Ethyl Canada Limited) are illustrative of viscosity index improvers having high shear stability.

Pour Point Depressants

Another useful type of additive which can be included in compositions of this invention is one or more pour point depressants. The use of pour point depressants in oil-base compositions to improve the low temperature properties of the compositions is well known to the art. See, for example, the books *Lubricant Additives* by C. V. Smalheer and R. Kennedy Smith (Lezius-Hiles Co. Publishers, Cleveland, Ohio, 1967); *Gear and Transmission Lubricants* by C. T. Boner (Reinhold Publishing Corp., New York, 1964); and *Lubricant Additives* by M. W. Ranney (Noyes Data Corporation, New Jersey, 1973). Among the types of compounds which function satisfactorily as pour point depressants in the compositions of this invention are polymethacrylates, polyacrylates, condensation products of haloparaffin waxes and aromatic compounds, and vinyl carboxylate polymers. Also useful as pour point depressants are terpolymers made by polymerizing a dialkyl fumarate, vinyl ester of a fatty acid and a vinyl alkyl ether. Techniques for preparing such polymers and their uses are disclosed in U.S. Pat. No. 3,250,715.

Other Metal Corrosion Inhibitors

In order to protect such metals as lead, cadmium, aluminum, magnesium, silver, zinc and alloys thereof, etc., special corrosion inhibitors can be used. These include such substances as gallic acid esters, phthalic acid esters, and the like.

The above descriptions of the various types of other additives which can be used in the compositions of this invention is not to be construed as limitive, as many other types of additives can be used in such compositions. The only requirements are that such other additives not excessively interfere adversely with the performance of the compositions of this invention and that they exhibit suitable compatibility with the additives otherwise being employed therein.

Base Oils

The ashless dispersants of this invention and the additive combinations of this invention can be incorporated in a wide variety of lubricants and functional fluids in effective amounts to provide suitable active ingredient concentrations. The base oils not only can be hydrocarbon oils of lubricating viscosity derived from petroleum (or tar sands, coal, shale, etc.), but also can be natural oils of suitable viscosities such as rapeseed oil, etc., and synthetic oils such as hydrogenated polyolefin oils; poly-α-olefins (e.g., hydrogenated or unhydrogenated α-olefin oligomers such as hydrogenated poly-1-decene); alkyl esters of dicarboxylic acids; complex esters of dicarboxylic acid, polyglycol and alcohol; alkyl esters of carbonic or phosphoric acids; polysilicones; fluorohydrocarbon oils; and mixtures of mineral, natural and/or synthetic oils in any proportion, etc. The term "base oil" for this disclosure includes all the foregoing.

The additive combinations of this invention can thus be used in lubricating oil and functional fluid compositions, such as automotive crankcase lubricating oils, automatic transmission fluids, gear oils, hydraulic oils, cutting oils, etc., in which the base oil of lubricating viscosity is a mineral oil, a synthetic oil, a natural oil such as a vegetable oil, or a mixture thereof, e.g. a mixture of a mineral oil and a synthetic oil.

Suitable mineral oils include those of appropriate viscosity refined from crude oil of any source including Gulf Coast, Midcontinent, Pennsylvania, California, Alaska, Middle East, North Sea and the like. Standard refinery operations may be used in processing the mineral oil. Among the general types of petroleum oils useful in the compositions of this invention are solvent neutrals, bright stocks, cylinder stocks, residual oils, hydrocracked base stocks, paraffin oils including pale oils, and solvent extracted naphthenic oils. Such oils and blends of them are produced by a number of conventional techniques which are widely known by those skilled in the art.

As is noted above, the base oil can consist essentially of or comprise a portion of one or more synthetic oils. Among the suitable synthetic oils are homo- and interpolymers of $C_2$-$C_{12}$ olefins, carboxylic acid esters of both monoalcohols and polyols, polyethers, silicones, polyglycols, silicates, alkylated aromatics, carbonates, thiocarbonates, orthoformates, phosphates and phosphites, borates and halogenated hydrocarbons. Representative of such oils are homo- and interpolymers of $C_2$-$C_{12}$ monoolefinic hydrocarbons, carbons, alkylated benzenes (e.g., dodecyl benzenes, didodecyl benzenes, tetradecyl benzenes, dinonyl benzenes, di-(2-ethylhexyl)benzenes, wax-alkylated naphthalenes); and polyphenyls (e.g., biphenyls, terphenyls). Alkylene oxide polymers and interpolymers and derivatives thereof where the terminal hydroxyl groups have been modified by esterification, etherification, etc., constitute another class of synthetic oils. These are exemplified by the oils prepared through polymerization of alkylene oxides such as ethylene oxide or propylene oxide, and the alkyl and aryl ethers of these polyoxyalkylene polymers (e.g., methyl polyisopropylene glycol ether having an average molecular weight of 1,000, diphenyl ether of polyethylene glycol having a molecular weight of 500–1,000, diethyl ether of polypropylene glycol having a molecular weight of 1,000–1,500) or mono- and polycarboxylic esters thereof, for example, the acetic acid ester, mixed $C_3$-$C_6$ fatty acid esters, or the $C_{13}$ Oxo acid diester of tetraethylene glycol.

Another suitable class of synthetic oils comprises the esters of dicarboxylic acids (e.g., phthalic acid, succinic acid, maleic acid, azelaic acid, suberic acid, sebacic acid, fumaric acid, adipic acid, linoleic acid dimer) with a variety of alcohols (e.g., butyl alcohol, hexyl alcohol, dodecyl alcohol, 2-ethylhexyl alcohol, ethylene glycol). Specific examples of these esters include dibutyl adipate, di(2-ethylhexyl) adipate, didodecyl adipate, di(tridecyl) adipate, di(2-ethylhexyl) sebacate, dilauryl sebacate, di-n-hexyl fumarate, dioctyl sebacate, diisooctyl azelate, diisodecyl azelate, dioctyl phthalate, didecyl phthalate, di(eicosyl) sebacate, the 2-ethylhexyl diester of linoleic acid dimer, and the complex ester formed by reacting one mole of sebacic acid with two moles of tetraethylene glycol and two moles of 2-ethylhexanoic acid.

Other esters which may be used include those made from $C_3$-$C_{18}$ monocarboxylic acids and polyols and polyol ethers such as neopentyl glycol, trimethylolpropane, pentaerythritol and dipentaerythritol. Trimethylol propane tripelargonate, pentaerythritol tetracaproate, the ester formed from trimethylolpropane, caprylic acid and sebacic acid, and the polyesters derived from a $C_4$-$C_{14}$ dicarboxylic acid and one or more aliphatic dihydric $C_3$-$C_{12}$ alcohols such as derived from azelaic acid or sebacic acid and 2,2,4-trimethyl-1,6-hexanediol serve as examples.

Silicon-based oils such as the polyalkyl-, polyaryl-, polyalkoxy-, or polyaryloxy-siloxane oils and silicate oils comprise another class of synthetic lubricants (e.g., tetraethyl silicate, tetraisopropyl silicate, tetra-(2-ethylhexyl) silicate, tetra-(p-tert-butylphenyl) silicate, poly(methyl)siloxanes, and poly(methylphenyl)siloxanes. Other synthetic lubricating oils include liquid esters of phosphorus-containing acids (e.g., tricresyl phosphate, trioctyl phosphate, triphenyl phosphite, and diethyl ester of decane phosphonic acid.

Also useful as base oils or as components of base oils are hydrogenated or unhydrogenated liquid oligomers of $C_6$–$C_{16}$ α-olefins, such as hydrogenated or unhydrogenated oligomers formed from 1-decene. Methods for the production of such liquid oligomeric 1-alkene hydrocarbons are known and reported in the literature. See for example U. S. Pat. Nos. 3,749,560; 3,763,244; 3,780,128; 4,172,855; 4,218,330; 4,902,846; 4,906,798; 4,910,355; 4,911,758; 4,935,570; 4,950,822; 4,956,513; and 4,981,578. Additionally, hydrogenated 1-alkene oligomers of this type are available as articles of commerce, e.g., under the trade designations ETHYLFLO 162, ETHYLFLO 164, ETHYLFLO 166, ETHYLFLO 168, ETHYLFLO 170, ETHYLFLO 174, and ETHYLFLO 180 poly-α-olefin oils (Ethyl Corporation; Ethyl Canada Limited; Ethyl S.A.). ETHYLFLO is a trademark of Ethyl Corporation. Blends of such materials can also be used in order to adjust the viscometrics of the given base oil. Suitable 1-alkene oligomers are also available from other suppliers. As is well known, hydrogenated oligomers of this type contain little, if any, residual ethylenic unsaturation.

Preferred oligomers are formed by use of a Friedel-Crafts catalyst (especially boron trifluoride promoted with water or a $C_{1-20}$ alkanol) followed by catalytic hydrogenation of the oligomer so formed using procedures such as are described in the foregoing U.S. patents.

Other catalyst systems which can be used to form oligomers of 1-alkene hydrocarbons, which, on hydrogenation, provide suitable oleaginous liquids include Ziegler catalysts such as ethyl aluminum sesquichloride with titanium tetrachloride, aluminum alkyl catalysts, chromium oxide catalysts on silica or alumina supports and a system in which a boron trifluoride catalyst oligomerization is followed by treatment with an organic peroxide.

It is also possible in accordance with this invention to utilize blends of one or more liquid hydrogenated 1-alkene oligomers in combination with other oleaginous materials having suitable viscosities, provided that the resultant blend has suitable compatibility and possesses the physical properties desired.

For some applications, for example use under conditions where oxidative or thermal degradation of the base oil is unlikely to be experienced, unhydrogenated 1-alkene oligomers can be used as the base oil or as a component in a base oil blend.

Likewise, various proprietary synthetic lubricants such as KETJENLUBE synthetic oil of Akzo Chemicals can be employed either as the sole base lubricant or as a component of the base lubricating oil.

Typical natural oils that may be used as base oils or as components of the base oils include castor oil, olive oil, peanut oil, rapeseed oil, corn oil, sesame oil, cottonseed oil, soybean oil, sunflower oil, safflower oil, hemp oil, linseed oil, tung oil, oiticica oil, jojoba oil, meadowfoam oil, and the like. Such oils may be partially or fully hydrogenated, if desired.

The fact that the base oils used in the compositions of this invention may be composed of (i) one or more mineral oils, (ii) one or more synthetic oils, (iii) one or more natural oils, or (iv) a blend of (i) and (ii), or (i) and (iii), or (ii) and (iii), or (i), (ii) and (iii) does not mean that these various types of oils are necessarily equivalents of each other. Certain types of base oils may be used in certain compositions for the specific properties they possess such as biodegradability, high temperature stability, non-flammability or lack of corrosivity towards specific metals (e.g. silver or cadmium). In other compositions, other types of base oils may be preferred for reasons of availability or low cost. Thus, the skilled artisan will recognize that while the various types of base oils discussed above may be used in the compositions of this invention, they are not necessarily functional equivalents of each other in every instance.

Proportions and Concentrations

In general, the components of the additive compositions of this invention are employed in the oleaginous liquids (e.g., lubricating oils and functional fluids) in minor amounts sufficient to improve the performance characteristics and properties of the base oil or fluid. The amounts of the components used in the base oil will vary in accordance with such factors as the viscosity characteristics of the base oil or fluid employed, the viscosity characteristics desired in the finished product, the service conditions for which the finished product is intended, and the performance characteristics desired in the finished product. However, generally speaking, the amounts of the components utilized in Embodiments A, B, C and D will fall in the ranges set forth hereinabove. The following concentrations (weight percent) of other components (on an active ingredients basis, i.e., excluding diluents which often are associated therewith) in the base oils or fluids are illustrative:

| | Typical Range | Preferred Range |
| --- | --- | --- |
| Amine salt of carboxy" ..id | 0–1 | 0.01–2 |
| Demulsifier | 0–0.5 | 0–0.2 |
| Cu corrosion inhibitor | 0–0.5 | 0.01–0.2 |
| Supplemental ashless dispersant | 0–3 | 0–2 |
| Antioxidant | 0–2 | 0–1 |
| Rust inhibitor | 0–1 | 0.02–0.5 |
| Antifoam agent | 0–0.3 | 0.0002–0.1 |
| Friction modifier | 0–2 | 0–1 |
| Seal swell agent | 0–20 | 0–10 |
| Viscosity index improver | 0–20 | 0–15 |
| Pour point depressant | 0–2 | 0–1 |
| Other metal corrosion inhibitors | 0–1 | 0–0.5 |

It is to be noted that some additives are multifunctional additives capable of contributing more than a single property to the blend in which they are used. Thus when employing a multi-functional additive component in the compositions of this invention, the amount used should of course be sufficient to achieve the function(s) and result(s) desired therefrom.

It will be appreciated that the individual components can be separately blended into the base oil or fluid or can be blended therein in various subcombinations, if desired. Moreover, such components can be blended in the form of separate solutions in a diluent. Except for viscosity index improvers and/or pour point depressants (which in many instances are blended apart from other components), it is preferable to blend the other selected components into the base oil by use of an additive concentrate of this invention, as this simplifies the blending operations, reduces the likelihood of blending errors, and takes advantage of the compatibility and solubility characteristics afforded by the overall concentrate.

The additive concentrates of this invention will contain the individual components in amounts proportioned to yield finished oil or fluid blends consistent with the concentrations tabulated above. In most cases, the additive concentrate will contain one or more diluents such as light mineral oils, to facilitate handling and blending of the concentrate. Thus concentrates containing up to 80% by weight of one or more diluents or solvents can be used.

The oleaginous liquids provided by this invention can be used in a variety of applications. For example, they can be employed as crankcase lubricants, gear oils, hydraulic fluids, manual transmission fluids, automatic transmission fluids, cutting and machining fluids, brake fluids, shock absorber fluids, heat transfer fluids, quenching oils, transformer oils, and the like. The compositions are particularly suitable for use as automotive and industrial gear oils.

Blending

To make the compositions of this invention, one either purchases or synthesizes each of the respective individual components to be used in the formulation or blending operation. Unless one is already in the commercial manufacture of one or more such components, it is usually simpler and thus preferable to purchase, to the extent possible, the ingredients to be used in the compositions of this invention. If it is desired to synthesize one or more components, use may be made of synthesis procedures referred to in the literature, including, but by no means limited to, the applicable references cited herein. In some cases, the components can be formed in situ by in situ reactions between or among components introduced into the mixture. For example, amine salts of monothiophosphoric acid esters can be formed in situ by introducing into the blending vessel a material such as sulfurized isobutylene and one or more amines, followed by the introduction of one or more dihydrocarbyl hydrogen phosphites.

The formulation or blending operations are relatively simple and involve mixing together in a suitable container or vessel, using a dry, inert atmosphere where necessary or desirable, appropriate proportions of the selected ingredients. Those skilled in the art are cognizant of and familiar with the procedures suitable for formulating and blending additive concentrates and lubricant compositions. Usually the order of addition of components to the blending tank or vessel is not critical provided of course, that the components being blended at any given time are not incompatible or excessively reactive with each other. Agitation such as with mechanical stirring equipment is desirable to facilitate the blending operation. Frequently it is helpful to apply sufficient heat to the blending vessel during or after the introduction of the ingredients thereto, so as to maintain the temperature at, say, 40°-60° C., and preferably no higher than about 60° C. Similarly, it is sometimes helpful to preheat highly viscous components to a suitable temperature even before they are introduced into the blending vessel in order to render them more fluid and thereby facilitate their introduction into the blending vessel and render the resultant mixture easier to stir or blend. Naturally the temperatures used during the blending operations should be controlled so as not to cause any significant amount of thermal degradation or unwanted chemical interactions.

When forming the lubricant compositions of this invention, it is usually desirable to introduce the additive ingredients into the base oil with stirring and application of mildly elevated temperatures, as this facilitates the dissolution of the components in the oil and achievement of product uniformity.

This invention is susceptible to considerable variation in its practice within the spirit and scope of the ensuing claims, the forms hereinbefore described constituting preferred embodiments thereof.

We claim:

1. A process for preparing a succinic derivative composition which comprises
(A) preparing a substituted succinic acylating agent by a process which comprises reacting (i) at least one substantially aliphatic polymer of at least one lower olefin, and (ii) an acidic reactant or a mixture of two or more acidic reactants represented by the general formula

wherein R and R' are independently —OH, —O-lower alkyl, a halogen atom, or taken together are a single oxygen atom; the process being characterized in that:
a) the substantially aliphatic polymer is comprised predominantly or entirely of polyisobutene, at least 50% of the polyisobutene content of such polymer having an end group represented by the formula

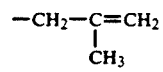

b) the mole ratio of said acidic reactant(s):said polymer(s) is at least 1:1;
c) the reaction mixture is maintai'  ' under superatmospheric pressure during at least a substantial portion of the reaction period; and
d) said acylating agent is characterized by having an average total tar rating as determined by the method described in the specification hereof that is at least 25% lower than the average total tar rating of a corresponding product made in the same way under the same reaction conditions using a polyisobutene containing up to 10% of the above-depicted end group; and
(B) reacting said acylating agent with a reactant selected from the group consisting of (1) at least one amine having at least one primary or secondary amino group, (2) at least one alcohol, and (3) a combination of at least one amine having at least one primary or secondary amino group and at least one alcohol, the components of (3) being reacted with said acylating agent concurrently or sequentially in any order.

2. A process as claimed in claim 1 wherein said reactant in (B) is (i) at least one polyamine having at least one primary amino group or (ii) at least one polyhydric alcohol or (iii) a combination of (i) and (ii), the components of (iii) being reacted with said acylating agent concurrently or sequentially in any order.

3. A process as claimed in claim 2 wherein the acidic reactant consists essentially of maleic anhydride and wherein the polymer consists essentially of polyisobutene.

4. A process as claimed in claim 2 wherein the polymer consists essentially of polyisobutene and at least 50% of the total polymer(s) is polyisobutene having said end group.

5. A process as claimed in claim 2 wherein the polymer consists essentially of polyisobutene and at least 75% of such polymer has said end group.

6. A process as claimed in claim 2 wherein the entire reaction of (A) or substantially the entire reaction of (A) is conducted under superatmospheric pressure.

7. A process as claimed in claim 2 wherein the entire reaction of (A) or substantially the entire reaction of (A) is conducted in a closed reaction system at superatmospheric pressure.

8. A process as claimed in claim 2 conducted such that the superatmospheric pressure on the reaction mixture in (A) decreases after passing through an initial peak pressure, and then increases to another elevated pressure.

9. A process as claimed in claim 8 wherein such elevated pressure is higher than the initial peak pressure.

10. A process as claimed in claim 2 wherein at least a substantial portion of the reaction of (A) is conducted at a pressure in the range of about 4 to about 50 psig.

11. A process as claimed in claim 2 wherein the temperature of the reaction mixture in the reaction of (A) is maintained in the range of about 200° to about 265° C. throughout substantially the entire reaction period of (A).

12. A process as claimed in claim 2 wherein the mole ratio of said acidic reactant(s): said polymer(s) is in the range of 1.1:1 to about 1.9:1.

13. A process as claimed in claim 2 wherein the acidic reactant consists essentially of maleic anhydride, wherein the mole ratio of maleic anhydride: said polymer(s) is in the range of 1.1:1 to about 1.9:1, and wherein unreacted maleic anhydride is recovered from the reaction mixture of (A).

14. A process as claimed in claim 2 wherein the acidic reactant consists essentially of maleic anhydride and wherein the polymer consists essentially of polyisobutene.

15. A process as claimed in claim 14 wherein at least 75% of the polyisobutene has said end group, wherein the entire reaction of (A) or substantially the entire reaction of (A) is conducted in a closed reaction system at superatmospheric pressure such that the superatmospheric pressure on the reaction mixture decreases after passing through an initial peak pressure, and then increases to another elevated pressure.

16. A process as claimed in claim 15 wherein said elevated pressure is higher than the initial peak pressure.

17. A process as claimed in claim 15 wherein the temperature of the reaction mixture in (A) is maintained in the range of about 200° to about 265° C. throughout substantially the entire reaction period of (A).

18. A process as claimed in claim 2 wherein the reaction of (i) and (ii) is conducted in the substantial absence of a thermal stabilizer.

19. A process as claimed in claim 2 wherein the succinic derivative composition formed in (B) is subjected to further reaction with at least one post-treating reactant.

20. A process as claimed in anyone of claims 1 through 19 wherein the mole ratio of said acidic reactant(s):said polymer(s) is such that the product contains in chemically combined form an average of less than 1.3 moles of said acid groups per mole of polymer chains chemically combined therewith.

21. A process for preparing polybutenyl succinimides which comprises reacting
(A) a substituted succinic acylating agent formed by a process which comprises reacting (i) at least one substantially aliphatic polymer of at least one lower olefin, and (ii) an acidic reactant or a mixture of two or more acidic reactants represented by the general formula

wherein R and R' are independently —OH, —O-lower alkyl, a halogen atom, or taken together are a single oxygen atom; the process being characterized in that:
a) the substantially aliphatic polymer is comprised predominantly or entirely of polyisobutene, at least 50% of the polyisobutene content of such polymer having an end group represented by the formula

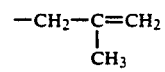

b) the mole ratio of said acidic reactant(s): said polymer(s) is at least 1:1;
c) the reaction mixture is maintained under superatmospheric pressure during at least a substantial portion of the reaction period; and
d) said acylating agent is characterized by having an average total tar rating as determined by the method described in the specification hereof that is at least 25% lower than the average total tar rating of a corresponding product made in the same way under the same reaction conditions using a polyisobutene containing up to 10% of the above-depicted end group; and
(B) at least one polyamine.

22. A process as claimed in claim 21 wherein said polyamine is at least one alkylene polyamine selected from ethylene or propylene diamines, diethylene triamine, triethylene tetramine, tetraethylene pentamine, and pentaethylene hexamine.

23. A process as claimed in claim 21 wherein said polyamine is a mixture of straight chain, branched chain, and cyclic polyethylene polyamines having an overall approximate composition falling in the range of triethylene tetramine to pentaethylene hexamine.

24. A carboxylic derivative composition produced by reacting at least one substituted succinic acylating agent with a reactant selected from the group consisting of (1) at least one amine having at least one primary or secondary amino group, (2) at least one alcohol, and (3) a combination of at least one amine having at least one primary or secondary amino group and at least one alcohol, the components of (3) being reacted with said at least one substituted succinic acylating agent concurrently or sequentially in any order, said at least one succinic acylating agent being prepared by reacting (i) at least one substantially aliphatic polymer of at least one lower olefin, and (ii) an acidic reactant or a mixture of two or more acidic reactants represented by the general formula

R—CO—CH=CH—CO—R' wherein R and R' are independently —OH, —O-lower alkyl, a halogen atom, or taken together are a single oxygen atom; the process of preparing said at least one succinic acylating agent being characterized in that:
a) the substantially aliphatic polymer is comprised predominantly or entirely of polyisobutene, at least 50% of the polyisobutene content of such polymer having an end group represented by the formula $$-CH_2-\underset{\underset{CH_3}{|}}{C}=CH_2$$

b) the mole ratio of said acidic reactant(s):said polymer(s) is at least 1:1; and
c) the reaction mixture is maintained under superatmospheric pressure during at least a substantial portion of the reaction period; and
d) said acylating agent is characterized by having an average total tar rating as determined by the method described in the specification hereof that is at least 25% lower than the average total tar rating of a corresponding product made in the same way under the same reaction conditions using a polyisobutene containing up to 10% of the above-depicted end group.

25. A composition of claim 24 wherein said carboxylic derivative composition is produced by reaction between said succinic acylating agent and at least one polyamine.

26. A composition of claim 24 wherein said carboxylic derivative composition is produced by reaction between said succinic acylating agent and at least one alkylene polyamine.

27. A composition of claim 24 wherein said carboxylic derivative composition is produced by reaction between said succinic acylating agent and a mixture of straight chain, branched chain, and cyclic polyethylene polyamines having an overall approximate composition falling in the range of triethylene tetramine to pentaethylene hexamine.

28. A composition of claim 24 wherein said carboxylic derivative composition is produced by reaction between said succinic acylating agent and at least one polyhydric alcohol.

29. A composition of claim 24 wherein said carboxylic 2 derivative composition is produced by reaction between said succinic acylating agent and at least one polyol.

30. A composition of claim 24 wherein said carboxylic derivative composition is produced by reaction between said succinic acylating agent and at least one polyamine and at least one polyhydric alcohol.

31. A composition of any one of claims 24 through 30 wherein the succinic acylating agent used in producing said carboxylic derivative compositions is further characterized by having a succination ratio of less than 1.3.

32. A composition as claimed in claim 24 wherein the succinic acylating agent used in producing said carboxylic derivative composition is further characterized by having, after removal of residual acidic reactant or reactants, an acid number of at least 0.7.

33. A composition as claimed in claim 32 wherein said acid number is at least 0.9.

34. A carboxylic derivative composition of claim 24 in admixture with at least one oil of lubricating viscosity or at least one hydrocarbonaceous liquid fuel in weight proportions falling in the range of about 0.1:99.9 to about 99.9:0.1.

* * * * *

UNITED STATES PATENT AND TRADEMARK OFFICE
CERTIFICATE OF CORRECTION

PATENT NO. : 5,137,980
DATED : August 11, 1992
INVENTOR(S) : David J. DeGonia, Paul G. Griffin It is certified that error appears in the above-indentified patent and that said Letters Patent is hereby corrected as shown below:

Column 68, line 16, "2 derivative" should read --derivative--

Signed and Sealed this

First Day of March, 1994

BRUCE LEHMAN

Attest:

Attesting Officer

Commissioner of Patents and Trademarks